United States Patent
Cosentino et al.

(10) Patent No.: US 7,945,451 B2
(45) Date of Patent: May 17, 2011

(54) REMOTE MONITORING SYSTEM FOR AMBULATORY PATIENTS

(75) Inventors: Daniel L. Cosentino, Minnetonka, MN (US); Louis C. Cosentino, Excelsior, MN (US)

(73) Assignee: Cardiocom, LLC, Chanhassen, MN (US)

( * ) Notice: Subject to any disclaimer, the term of this patent is extended or adjusted under 35 U.S.C. 154(b) by 1317 days.

(21) Appl. No.: 10/093,948

(22) Filed: Mar. 7, 2002

(65) Prior Publication Data
US 2003/0083556 A1 May 1, 2003

Related U.S. Application Data

(63) Continuation-in-part of application No. 09/949,197, filed on Sep. 7, 2001, now Pat. No. 6,755,783, which is a continuation-in-part of application No. 09/293,619, filed on Apr. 16, 1999, now Pat. No. 6,290,646.

(51) Int. Cl.
*G06Q 10/00* (2006.01)
(52) U.S. Cl. .............................. 705/2; 600/300; 128/897
(58) Field of Classification Search .................. 705/2–3; 600/300; 128/897
See application file for complete search history.

(56) References Cited

U.S. PATENT DOCUMENTS

| | | | |
|---|---|---|---|
| 3,743,040 A | 7/1973 | Cosentino et al. ............. 177/126 |
| 3,925,762 A | 12/1975 | Heitlinger et al. ....... 340/870.09 |
| 4,531,527 A * | 7/1985 | Reinhold et al. .............. 600/509 |
| 4,576,244 A | 3/1986 | Zeigner et al. |
| RE32,361 E | 2/1987 | Duggan ......................... 128/696 |
| 4,712,562 A | 12/1987 | Ohayon et al. ................ 600/485 |
| 4,803,625 A | 2/1989 | Fu et al. |
| 4,838,275 A * | 6/1989 | Lee ................................ 600/483 |
| 4,899,758 A | 2/1990 | Finkelstein et al. ........... 600/485 |
| 4,947,858 A | 8/1990 | Smith ............................ 600/509 |
| 5,012,411 A | 4/1991 | Policastro et al. ............. 600/485 |
| 5,054,493 A | 10/1991 | Cohn et al. .................... 600/485 |
| 5,092,330 A | 3/1992 | Duggan ......................... 600/300 |
| 5,113,869 A | 5/1992 | Nappholz et al. |
| 5,241,966 A | 9/1993 | Finkelstein et al. ........... 600/485 |
| 5,307,263 A | 4/1994 | Brown .......................... 600/301 |

(Continued)

FOREIGN PATENT DOCUMENTS
DE 43 35 869 A 1 10/1994
(Continued)

OTHER PUBLICATIONS
International Search Report for International Application No. PCT/US 03/07099, 8 pp., Jul. 22, 2003.
(Continued)

*Primary Examiner* — Vanel Frenel
(74) *Attorney, Agent, or Firm* — Fulbright & Jaworski

(57) ABSTRACT

The monitoring device incorporates a memory device that is programmed with a set of question hierearchies. Each question hierarchy corresponds to a symptom and is composed of a set of questions. The question hierarchies may contain a logical structure so that certain questions will not be asked, depending upon a patient's answer to a preceeding question. A question hiearchy is invoked by a symptom identifier transmitted to the monitoring device by a remote computer. The remote computer may transmit a plurality of symptom identifiers to the monitoring device to cause the monitoring device to ask questions related to a plurality of symptoms. The set of symptoms inquired about may vary based upon the chronic disease afflicting the patient.

37 Claims, 28 Drawing Sheets

U.S. PATENT DOCUMENTS

| | | | |
|---|---|---|---|
| 5,331,549 A | 7/1994 | Crawford, Jr. | 600/513 |
| 5,390,238 A | 2/1995 | Kirk et al. | 379/106.02 |
| 5,402,794 A | 4/1995 | Wahlstrand et al. | 600/508 |
| 5,406,955 A | 4/1995 | Bledsoe et al. | 600/524 |
| 5,434,611 A | 7/1995 | Tamura | 725/116 |
| 5,437,285 A | 8/1995 | Verrier et al. | 600/515 |
| 5,441,047 A * | 8/1995 | David et al. | 600/483 |
| 5,522,396 A | 6/1996 | Langer et al. | |
| 5,549,117 A | 8/1996 | Tacklind et al. | |
| 5,553,609 A * | 9/1996 | Chen et al. | 600/301 |
| 5,553,623 A | 9/1996 | Ochs | 600/300 |
| 5,560,370 A | 10/1996 | Verrier et al. | 128/705 |
| 5,584,868 A | 12/1996 | Salo et al. | |
| 5,594,638 A | 1/1997 | Iliff | 395/203 |
| 5,635,060 A | 6/1997 | Hagen et al. | |
| 5,660,176 A | 8/1997 | Iliff | 128/630 |
| 5,673,691 A | 10/1997 | Abrams et al. | |
| 5,687,717 A | 11/1997 | Halpern et al. | 128/630 |
| 5,704,366 A | 1/1998 | Tacklind et al. | 600/529 |
| 5,711,297 A | 1/1998 | Iliff | 128/630 |
| 5,724,032 A | 3/1998 | Klein et al. | 341/50 |
| 5,724,968 A | 3/1998 | Iliff | 128/630 |
| 5,725,559 A | 3/1998 | Alt et al. | 607/5 |
| 5,743,267 A | 4/1998 | Nikolic et al. | 128/673 |
| 5,745,555 A | 4/1998 | Mark | |
| 5,758,652 A | 6/1998 | Nikolic | 128/673 |
| 5,771,511 A | 6/1998 | Kummer et al. | |
| 5,778,882 A | 7/1998 | Raymond et al. | 600/513 |
| 5,822,715 A | 10/1998 | Worthington et al. | 702/19 |
| 5,828,943 A | 10/1998 | Brown | 434/258 |
| 5,832,448 A | 11/1998 | Brown | 705/2 |
| 5,839,438 A | 11/1998 | Graettinger et al. | 128/630 |
| 5,842,997 A | 12/1998 | Verrier et al. | 600/518 |
| 5,843,139 A | 12/1998 | Goedeke et al. | 607/32 |
| 5,846,223 A | 12/1998 | Swartz et al. | 604/53 |
| 5,868,669 A | 2/1999 | Iliff | 600/300 |
| 5,876,353 A | 3/1999 | Riff | |
| 5,879,163 A | 3/1999 | Brown et al. | 434/236 |
| 5,890,128 A | 3/1999 | Diaz et al. | |
| 5,897,493 A | 4/1999 | Brown | 600/300 |
| 5,899,855 A | 5/1999 | Brown | 600/301 |
| 5,910,107 A | 6/1999 | Iliff | 600/300 |
| 5,911,687 A | 6/1999 | Sato et al. | 600/300 |
| 5,913,310 A | 6/1999 | Brown | 128/897 |
| 5,918,603 A | 7/1999 | Brown | 128/897 |
| 5,931,791 A | 8/1999 | Saltzstein et al. | 600/513 |
| 5,933,136 A | 8/1999 | Brown | 345/327 |
| 5,935,060 A * | 8/1999 | Iliff | 600/300 |
| 5,951,300 A | 9/1999 | Brown | 434/236 |
| 5,957,861 A | 9/1999 | Combs et al. | |
| 5,960,403 A | 9/1999 | Brown | 705/2 |
| 5,985,559 A | 11/1999 | Brown | 435/6 |
| 5,987,519 A | 11/1999 | Peifer et al. | 709/230 |
| 5,997,476 A * | 12/1999 | Brown | 600/300 |
| 6,007,493 A | 12/1999 | Ericksen et al. | 600/508 |
| 6,022,315 A | 2/2000 | Iliff | 600/300 |
| 6,024,699 A | 2/2000 | Surwit et al. | |
| 6,032,119 A | 2/2000 | Brown et al. | 705/2 |
| 6,038,465 A | 3/2000 | Melton, Jr. | |
| 6,045,513 A | 4/2000 | Stone et al. | 600/508 |
| 6,071,236 A | 6/2000 | Iliff | 600/300 |
| 6,080,106 A | 6/2000 | Lloyd et al. | 600/300 |
| 6,085,162 A | 7/2000 | Cherny | 704/277 |
| 6,101,478 A | 8/2000 | Brown | 705/2 |
| 6,113,540 A | 9/2000 | Iliff | 600/300 |
| 6,144,837 A | 11/2000 | Quy | 434/307 R |
| 6,167,362 A | 12/2000 | Brown et al. | |
| 6,168,563 B1 | 1/2001 | Brown | 600/301 |
| 6,234,964 B1 | 5/2001 | Iliff | |
| 6,240,393 B1 | 5/2001 | Brown | |
| 6,246,992 B1 | 6/2001 | Brown | 705/2 |
| 6,248,065 B1 | 6/2001 | Brown | 600/300 |
| 6,270,456 B1 | 8/2001 | Iliff | 600/300 |
| 6,290,646 B1 | 9/2001 | Cosentino et al. | 600/300 |
| 6,328,699 B1 | 12/2001 | Eigler et al. | |
| 6,354,996 B1 | 3/2002 | Drinan et al. | 600/300 |
| 6,454,705 B1 | 9/2002 | Cosentino et al. | 600/300 |
| 6,723,045 B2 | 4/2004 | Cosentino et al. | 600/300 |
| 6,755,783 B2 | 6/2004 | Cosentino et al. | 600/300 |
| 6,849,045 B2 | 2/2005 | Iliff | |
| 7,127,290 B2 | 10/2006 | Girouard et al. | |
| 7,433,853 B2 | 10/2008 | Brockway et al. | |
| 7,577,475 B2 | 8/2009 | Cosentino et al. | |
| 2001/0053875 A1 | 12/2001 | Iliff | 600/300 |
| 2002/0133502 A1 | 9/2002 | Rosenthal et al. | |
| 2004/0102685 A1 | 5/2004 | Cosentino et al. | |
| 2004/0117204 A1 | 6/2004 | Mazar et al. | |
| 2004/0122297 A1 | 6/2004 | Stahmann et al. | |
| 2004/0147969 A1 | 7/2004 | Mann et al. | |
| 2004/0172080 A1 | 9/2004 | Stadler et al. | |
| 2004/0225533 A1 | 11/2004 | Cosentino et al. | |
| 2005/0015115 A1 | 1/2005 | Sullivan et al. | |
| 2005/0172021 A1 | 8/2005 | Brown | |
| 2006/0015017 A1 | 1/2006 | Cosentino et al. | |
| 2006/0030890 A1 | 2/2006 | Cosentino et al. | |
| 2006/0064030 A1 | 3/2006 | Cosentino et al. | |
| 2007/0021979 A1 | 1/2007 | Cosentino et al. | |
| 2007/0155588 A1 | 7/2007 | Stark et al. | |
| 2009/0234916 A1 | 9/2009 | Cosentino et al. | |

FOREIGN PATENT DOCUMENTS

| | | |
|---|---|---|
| EP | 0 251 520 A2 | 1/1988 |
| JP | 09173304 | 7/1997 |
| WO | WO 98/40835 | 9/1998 |
| WO | WO 98/50873 | 11/1998 |
| WO | WO 00/62662 | 10/2000 |
| WO | WO 01/21065 A1 | 3/2001 |
| WO | WO 01/22343 A2 | 3/2001 |
| WO | WO 01/39089 A1 | 5/2001 |
| WO | WO 03/075756 A1 | 9/2003 |

OTHER PUBLICATIONS

Lüthje, L. et al., "Detection of heart failure decompensation using intrathoracic impedance monitoring by a triple-chamber implantable defibrillator," *Heart Rhythm*, vol. 2, No. 9, pp. 997-999 (Sep. 2005).

"Thin-Link: Like Having a Personal Coach and Dietitian in Your Home Every Day,"http://web.archive.org/web/20041009141519/www.thin-link.com/program_weightloss.html, 2 pages (Date Printed Aug. 31, 2005).

Teixeira, P. et al., "Weight Loss Readiness in Middle-Aged Women: Psychosocial Predictors of Success for Behavioral Weight Reduction," *Journal of Behavioral Medicine*, vol. 25, No. 6, pp. 499-523 (Dec. 2002).

Patel, U. et al., "A Computer-Based, Automated, Telephonic System to Monitor Patient Progress in the Home Setting", *Journal of Medical Systems*, vol. 16, Nos. 2/3, pp. 101-112 (1992).

Yazolino, L., (title not legible), *Medical Electronics*, 4 pages (Sep. 1998).

"Telemedicine NEW: BP-TEL™ Transtelephonic Bloos Pressure: Your Partner In Telemedicine", http://www.aerotel.com/telemed/, 2 pgs. (Feb. 6, 2001) last updated.

"Telemedicine, Your Partner in Telemedicine", Aerotel Medical Systems, Ltd., Internet at http://www.aerotel.com/telemed/under.html, last updated Sep. 5, 1998.

"Technology to Help Meet Standards and Reduce Costs", Alere Medical Incorporated, 6 pages (1998).

\* cited by examiner

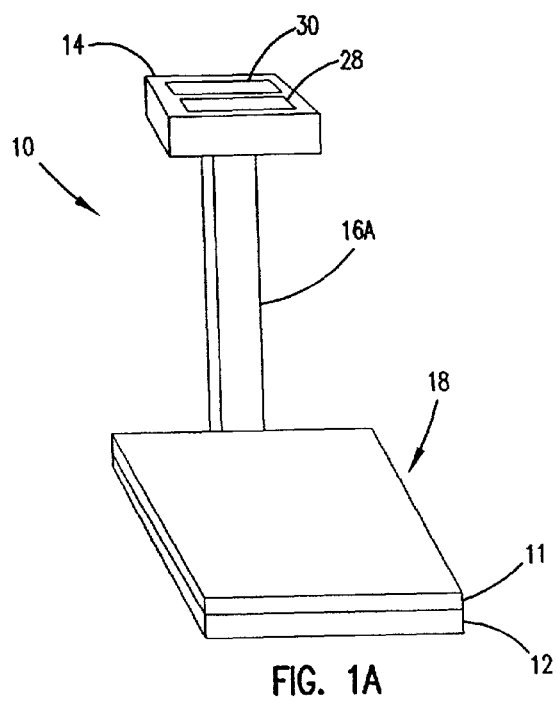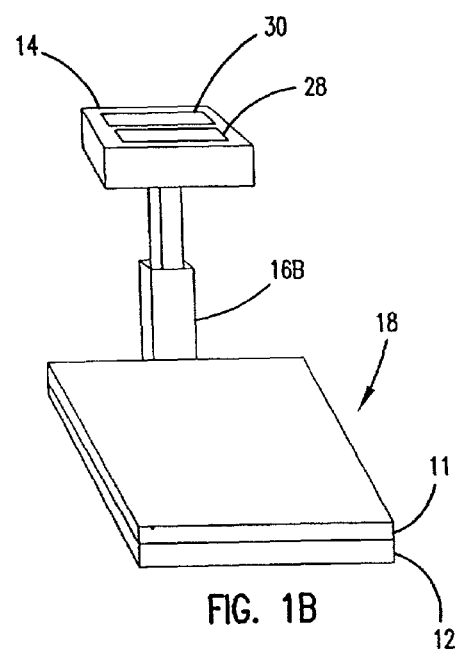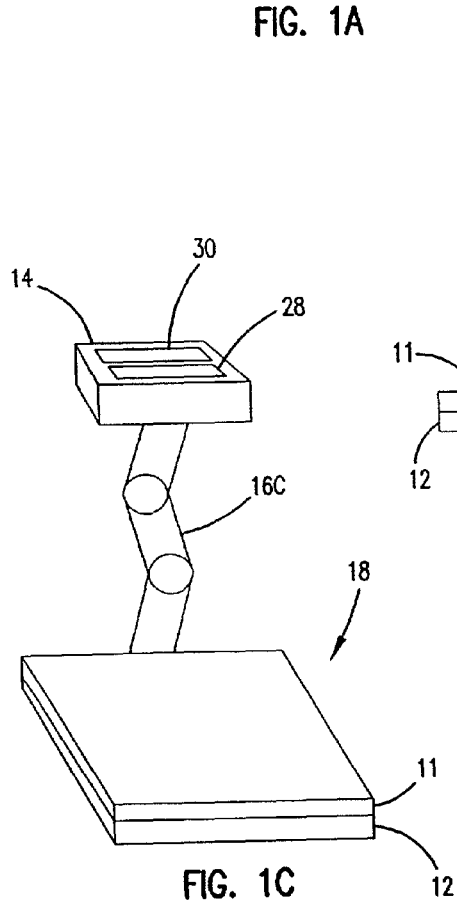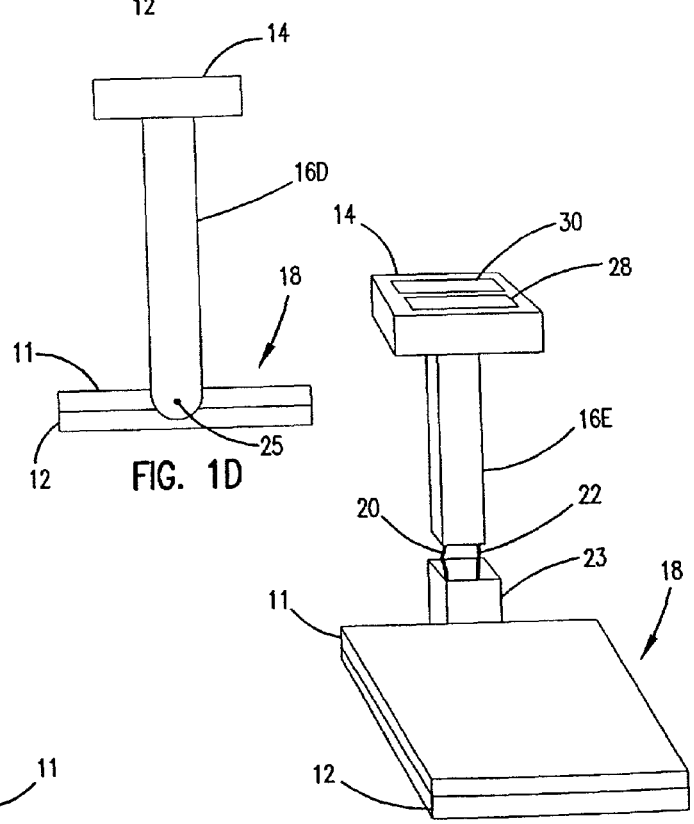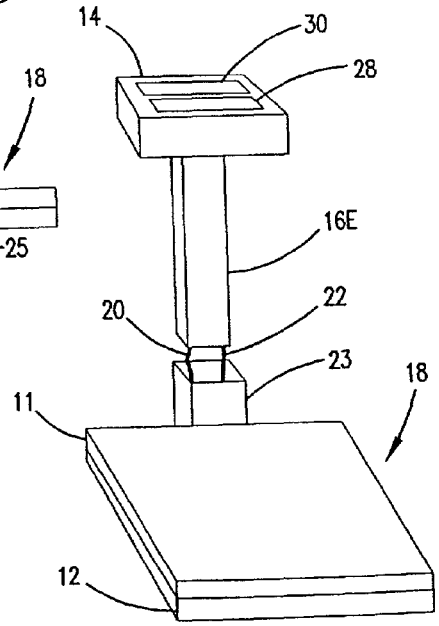

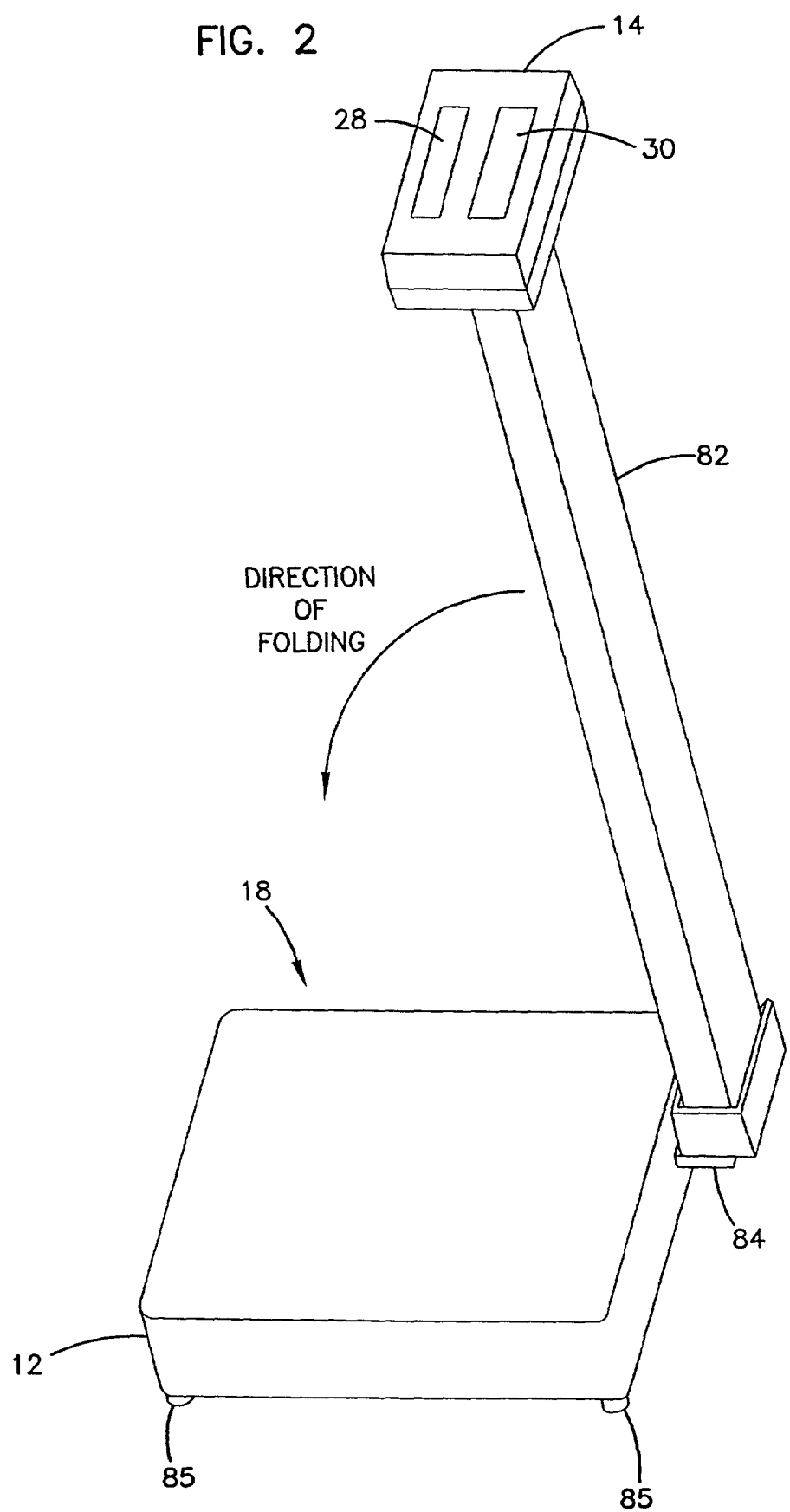

REMOTE MONITORING SYSTEM FOR AMBULATORY PATIENTS

RELATED APPLICATIONS

This application is a continuation-in-part of U.S. application Ser. No. 09/949,197 filed on Sep. 7, 2001 now U.S. Pat. No. 6,755,783, entitled "APPARATUS AND METHOD FOR TWO-WAY COMMUNICATION IN A DEVICE FOR MONITORING AND COMMUNICATING WELLNESS PARAMETERS OF AMBULATORY PATIENTS," which is a continuation-in-part of U.S. application Ser. No. 09/293,619 filed on Apr. 16, 1999 (which issued Sep. 18, 2001 as U.S. Pat. No. 6,290,646) entitled "APPARATUS AND METHOD FOR MONITORING AND COMMUNICATING WELLNESS PARAMETERS OF AMBULATORY PATIENTS," both of which are hereby incorporated by reference in its entirety.

BACKGROUND

There is a need in the medical profession for an apparatus and method capable of monitoring and transmitting physiological and wellness parameters of ambulatory patients to a remote site where a medical professional caregiver evaluates such physiological and wellness parameters. Specifically, there is a need for an interactive apparatus that is coupled to a remote computer such that a medical professional caregiver can supervise and provide medical treatment to remotely located ambulatory patients.

There is needed an apparatus that monitors and transmits physiological and wellness parameters of ambulatory patients to a remote computer, whereby a medical professional caregiver evaluates the information and provokes better overall health care and treatment for the patient. Accordingly, such an apparatus can be used to prevent unnecessary hospitalizations of such ambulatory patients.

Also, there is needed an apparatus for monitoring and transmitting such physiological and wellness parameters that is easy to use and that is integrated into a single unit. For example, there is a need for an ambulatory patient monitoring apparatus that comprises: a transducing device for providing electronic signals representative of measured physiological parameters, such as weight; an input/output device; and a communication device as a single integrated unit that offers ambulatory patients ease of use, convenience and portability.

Patients suffering from chronic diseases, such as chronic heart failure, will benefit from such home monitoring apparatus. These patients normally undergo drug therapy and lifestyle changes to manage their medical condition. In these patients, the medical professional caregiver monitors certain wellness parameters and symptoms including: weakness, fatigue, weight gain, edema, dyspnea (difficulty breathing or shortness of breath), nocturnal cough, orthopnea (inability to lie flat in bed because of shortness of breath), and paroxysmal nocturnal dyspnea (awakening short of breath relieved by sitting or standing); and body weight to measure the response of drug therapy. Patients will also benefit from daily reminders to take medications (improving compliance), reduce sodium intake and perform some type of exercise. With the information received from the monitoring device, the medical professional caregiver can determine the effectiveness of the drug therapy, the patient's condition, whether the patient's condition is improving or whether the patient requires hospitalization or an office consultation to prevent the condition from getting worse.

Accordingly, there is needed an apparatus and method for monitoring the patients from a remote location, thus allowing medical professional caregivers to receive feedback of the patient's condition without having to wait until the patient's next office visit. In addition, there is needed an apparatus and method that allows medical professional caregivers to monitor and manage the patient's condition to prevent the rehospitalization of such patient, or prevent the patient's condition from deteriorating to the point where hospitalization would be required. As such, there are social as well as economic benefits to such an apparatus and method.

The patient receives the benefits of improved health when the professional caregiver is able to monitor and quickly react to any adverse medical conditions of the patient or to any improper responses to medication. Also, society benefits because hospital resources will not be utilized unnecessarily.

As a group, patients suffering from chronic heart failure are the most costly to treat. There are approximately 5 million patients in the U.S.A. and 15 million worldwide with chronic heart failure. The mortality rate of patients over 65 years of age is 50%. Of those that seek medical help and are hospitalized, 50% are rehospitalized within 6 months. Of these, 16% will be rehospitalized twice. The patients that are hospitalized spend an average of 9.1 days in the hospital at a cost of $12,000.00 for the period. Accordingly, there is a need to reduce the rehospitalization rate of chronic heart failure patients by providing improved in-home patient monitoring, such as frequently monitoring the patient's body weight and adjusting the drug therapy accordingly.

Approximately 60 million American adults ages 20 through 74 are overweight. Obesity is a known risk factor for heart disease, high blood pressure, diabetes, gallbladder disease, arthritis, breathing problems, and some forms of cancer such as breast and colon cancer. Americans spend $33 billion dollars annually on weight-reduction products and services, including diet foods, products and programs.

There is a need in the weight management profession for an apparatus and method capable of monitoring and transmitting physiological and wellness parameters of overweight/obese patients to a remote site where a weight management professional or nutritionist evaluates such physiological and wellness parameters. Specifically, there is a need for an interactive apparatus that is coupled to a remote computer such that a weight management professional or nutritionist can supervise and provide nutritional guidance to remotely located individuals.

The apparatus allows overweight individuals to participate in a weight loss/management program with accurate weight monitoring from home. The apparatus improves the convenience for the individual participant by eliminating the need to constantly commute to the weight management center and "weigh-in." Furthermore, the individual can participate in a weight management program while under professional supervision from the privacy and comfort of their own home. Moreover, the apparatus allows the weight management professional to intervene and adapt the individuals diet and exercise routine based on the weight and wellness information received.

For the foregoing reasons, there is a need for an apparatus, system and method capable of monitoring and transmitting physiological and wellness parameters of ambulatory patients, such as body weight, to a remote location where a medical professional caregiver, weight management professional or nutritionist can evaluate and respond to the patient's medical wellness condition.

SUMMARY

Against this backdrop the present invention was created. A health care device for monitoring a health condition of an ambulatory patient may include a display for presenting questions to the patient. Additonally, it may include an input device permitting the patient to enter answers to the questions. Further, it may include a microprocessor operably coupled to the display and the input device. A read-only memory device may be operably coupled to the microprocessor. The read-only memory device may store a plurality of question hierarchies, with each hierarchy of questions corresponding to each of a plurality of symptoms. A communication device may be operably coupled to the microprocessor. The microprocessor may be programmed to receive a symptom identifier via the communication device. Based upon the symptom identifier, it may be programmed to ask a first question from the hierarchy of questions corresponding to the symptom identified by the symptom identifier. It may also be programmed to receive an answer to the first question via the input device. Finally, it may be programmed to make a decision regarding whether to ask a subsequent question from the hierarchy, based upon the answer to the first question.

According to another embodiment of the invention, a method for monitoring a health condition of an ambulatory patient may include receiving a symptom identifier. Thereafter, a question is retrieved from a hierarchy of questions stored in a read-only memory device. The hierarchy corresponds to a symptom identified by the symptom identifier. The retrieved question is asked to the patient. Next, an answer to the question is received from the patient. Thereafter, a decision regarding whether to ask a subsequent question from the hierarchy is made, based upon the answer to the question. The memory device stores a plurality of question hierarchies, with each hierarchy of questions corresponding to each of a plurality symptoms.

According to yet another embodiment of the invention, a method for monitoring a health condition of an ambulatory patient may include transmitting a symptom identifier to a health care device containing a read-only memory that stores a plurality of question hierarchies. Each hierarchy of questions corresponds to each of a plurality of symptoms. The transmission causes the health care device to ask to the patient one or more questions from a hierarchy corresponding to the symptom identified by the symptom identifier.

According to yet another embodiment of the invention, a method of analyzing a set of answers to questions drawn from a plurality of question hierarchies may include assigning a point value to each question within each hierarchy. The point value may be earned if the question to which it is assigned is answered in accordance with a pre-defined answer. A total point value, which is a sum of the point values assigned to each question that was asked, may be determined. Additionally, an earned point value, which is a sum of all points earned, may be determined. Then, a ratio between the earned point value and the total point value may be determined. Finally, a health care provider may be notified if the ratio exceeds a threshold.

According to yet another embodiment of the invention, a method of analyzing a set of answers to questions drawn from a plurality of question hierarchies may include assigning a point value to each question within each hierarchy. The point value may be earned if the question to which it is assigned is answered in accordance with a pre-defined answer. A threshold value is assigned to each hierarchy of questions. Also, the number of points earned in each question hierarchy is determined, based upon the answers. Finally, a health care provider may be notified, if more than a pre-defined number of points are earned within more than a pre-defined number of question hierarchies.

According to yet another embodiment of the invention, a health care system for monitoring a health condition of an ambulatory patient may include a health care device and a central computer system. The health care device may include a display for presenting questions to the patient. It may also include an input device permitting the patient to enter answers to the questions. A microprocessor may be operably coupled to the display and the input device. A read-only memory device may be operably coupled to the microprocessor. The read-only memory device may store a plurality of question hierarchies, with each hierarchy of questions corresponding to each of a plurality of symptoms. A communication device may be operably coupled to the microprocessor. The microprocessor may be programmed to receive a symptom identifier via the communication device. Based upon the symptom identifier, the microprocessor may ask a first question from the hierarchy of questions corresponding to the symptom identified by the symptom identifier. An answer to the first question may be reveived via the input device. Based upon the answer to the first question, a decision regarding whether to ask a subsequent question from the hierarchy may be made. The central computer system may be in communication with the microprocessor of the health care device. The central computer system may be programmed to transmit the symptom identifier to the microprocessor, thereby causing the microprocessor to ask one or more questions within the hierarchies corresponding to the symptom identified by the symptom identifier. A point value may be assigned to each question within each hierarchy. Based upon the assigned point values, it may be determine whether the patient is in need of care.

BRIEF DESCRIPTION OF THE DRAWINGS

These and other features, aspects and advantages of the invention will become better understood with regard to the following description, appended claims and accompanying drawings where:

FIGS. 1A-E illustrates several embodiments of the monitoring apparatus in accordance with the invention;

FIG. 2 illustrates a monitoring apparatus with a support member in accordance with one embodiment of the invention;

DESCRIPTION

Figure 3:
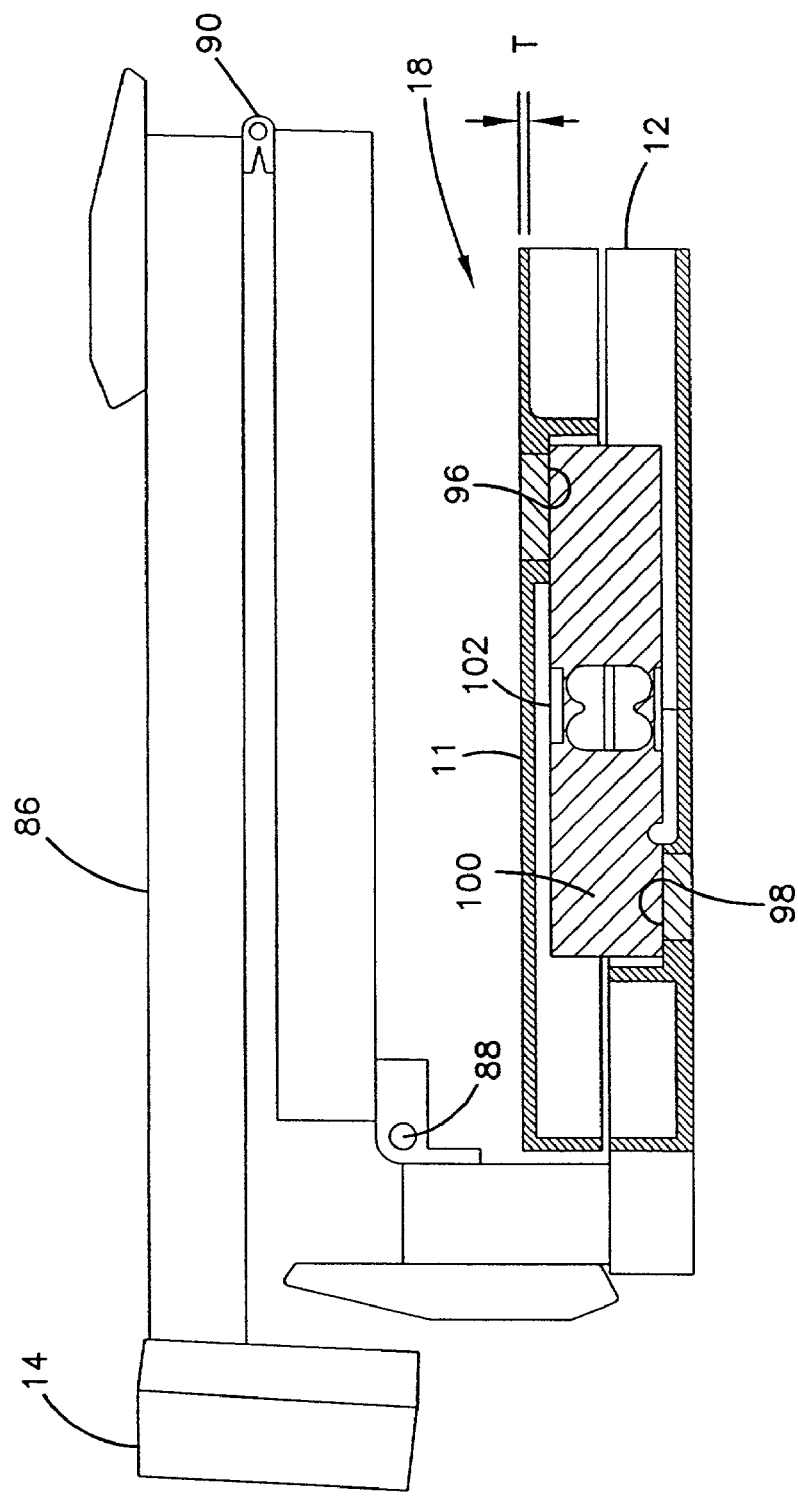
FIG. 3 illustrates a monitoring apparatus with a support member in accordance with one embodiment of the invention.

The embodiments of the invention described herein are implemented as a medical apparatus, system and method capable of monitoring wellness parameters and physiological data of ambulatory patients and transmitting such parameters and data to a remote location. At the remote location a medical professional caregiver monitors the patient's condition and provides medical treatment as may be necessary.

The monitoring device incorporates transducing devices for converting the desired measured parameters into electrical signals capable of being processed by a local computer or microprocessor system. The device interacts with the ambulatory patient and then, via an electronic communication device such as a modem, transmits the measured parameters to a computer located at a remote site. At the remote location the various indicia of the ambulatory patient's condition are monitored and analyzed by the medical professional caregiver. To provide the ambulatory patient with an added level of convenience and ease of use, such monitoring device is contained in a single integrated package. Communication is established between the monitoring apparatus and a remote computer via modem and other electronic communication devices that are generally well known commercially available products. At the remote location, the caregiver reviews the patient's condition based on the information communicated (e.g. wellness parameters and physiological data) and provokes medical treatment in accordance with such information.

Referring now to FIG. 1A, as this embodiment of the invention is described herein, an integrated monitoring apparatus is shown generally at 10. The integrated monitoring apparatus 10 includes an electronic scale 18. The electronic scale 18 further includes a top plate 11 and a base plate 12. The integrated monitoring apparatus 10 further includes a housing 14 and a support member 16A. The base plate 12 is connected to the housing 14 through the support member 16A. The housing 14 further includes output device(s) 30 and input device(s) 28. The apparatus 10 is integrated as a single unit with the support member coupling the base plate 12 and the housing 14, thus providing a unit in a one piece construction.

It will be appreciated that other physiological transducing devices can be utilized in addition to the electronic scale 18. For example, blood pressure measurement apparatus and electrocardiogram (EKG) measurement apparatus can be utilized with the integrated monitoring apparatus 10 for recordation and/or transmission of blood pressure and EKG measurements to a remote location. It will be appreciated that other monitoring devices of physiological body functions that provide an analog or digital electronic output may be utilized with the monitoring apparatus 10.

Referring to FIGS. 1B, 1C, 1D and 1E it will be appreciated that the support member 16A (FIG. 1A) can be made adjustable. For example, FIG. 1B illustrates an embodiment of the invention utilizing a telescoping support member 16B. Likewise, FIG. 1C illustrates an embodiment of the invention utilizing a folding articulated support member 16C. FIG. 1D illustrates yet another embodiment of the invention utilizing support member 16D that folds at a pivot point 25 located at its base. It will also be appreciated that other types of articulated and folding support members may be utilized in other embodiments of the invention. For example, FIG. 1E illustrates an embodiment of the invention providing a support member 16E that is removably insertable into a socket 23. A cable 22 is passed through the support member 16E to carry electrical signals from the electronic scale 18 to the housing 14 for further processing. A tether 20 is provided to restrain the movement of the support member 16E relative to the base plate 12 once the it is removed from the socket 23.

FIG. 2 illustrates an embodiment of the invention where the support member 82 folds about pivot point 84. Folding the integrated monitoring apparatus about pivot point 84 provides a convenient method of shipping, transporting or moving the apparatus in a substantially horizontal orientation. The preferred direction of folding is indicated in the figure, however, the support member 82 can be made to fold in either direction. Furthermore, an embodiment of the invention provides rubber feet 85 underneath the base plate 12.

Furthermore, FIG. 3 illustrates one embodiment of the invention providing an articulated, folding support member 86. The support member 86 folds at two hinged pivot points 88, 90. Also illustrated is a sectional view of the scale 18, top plate 11, base plate 12, load cell 100 and strain gage 102.

Figure 4:
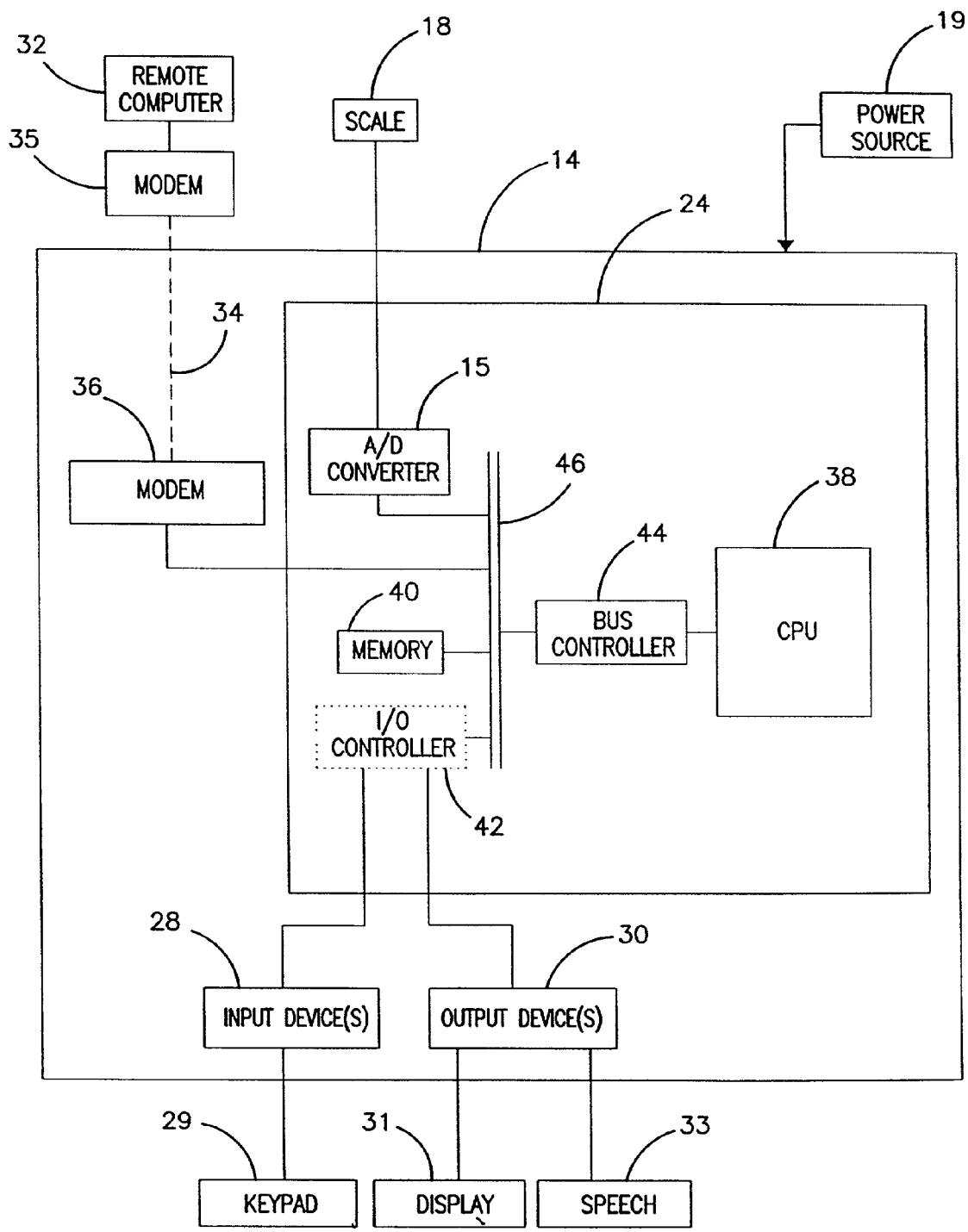
FIG. 4 is a functional block diagram of a microprocessor system forming an environment in which one embodiment of the invention may be employed.

Referring now to FIG. 4, a microprocessor system 24 including a CPU 38, a memory 40, an optional input/output (1/0) controller 42 and a bus controller 44 is illustrated. It will be appreciated that the microprocessor system 24 is available in a wide variety of configurations and is based on CPU chips such as the Intel, Motorola or Microchip PIC family of microprocessors or microcontrollers.

It will be appreciated by those skilled in the art that the monitoring apparatus requires an electrical power source 19 to operate. As such, the monitoring apparatus may be powered by: ordinary household A/C line power, DC batteries or rechargeable batteries. Power source 19 provides electrical power to the housing for operating the electronic devices. A power source for operating the electronic scale 18 is generated within the housing, however those skilled in the art will recognize that a separate power supply may be provided or the power source 19 may be adapted to provide the proper voltage or current for operating the electronic scale 18.

The housing 14 includes a microprocessor system 24, an electronic receiver/transmitter communication device such as a modem 36, an input device 28 and an output device 30. The modem 36 is operatively coupled to the microprocessor system 24 via the electronic bus 46, and to a remote computer 32 via a communication network 34 and modem 35. The communication network 34 being any communication network such as the telephone network, wide area network or Internet. It will be appreciated that the modem 36 is a generally well known commercially available product available in a variety of configurations operating at a variety of BAUD rates. In one embodiment of the invention the modem 36 is asynchronous, operates at 2400 BAUD and is readily available off-the-shelf from companies such as Rockwell or Silicon Systems Inc. (SSI).

It will be appreciated that output device(s) 30 may be interfaced with the microprocessor system 24. These output devices 30 include a visual electronic display device 31 and/or a synthetic speech device 33. Electronic display devices 31 are well known in the art and are available in a variety of technologies such as vacuum fluorescent, liquid crystal or Light Emitting Diode (LED). The patient reads alphanumeric data as it scrolls on the electronic display device 31. Output devices 30 include a synthetic speech output device 33 such as a Chipcorder manufactured by ISD (part No. 4003). Still, other output devices 30 include pacemaker data input devices, drug infusion pumps or transformer coupled transmitters.

It will be appreciated that input device(s) 28 may be interfaced with the microprocessor system 24. In one embodiment of the invention an electronic keypad 29 is provided for the patient to enter responses into the monitoring apparatus. Patient data entered through the electronic keypad 29 may be scrolled on the electronic display 31 or played back on the synthetic speech device 33.

The microprocessor system 24 is operatively coupled to the modem 36, the input device(s) 28 and the output device(s) 30. The electronic scale 18 is operatively coupled to the central system 24. Electronic measurement signals from the electronic scale 18 are processed by the A/D converter 15. This digitized representation of the measured signal is then interfaced to the CPU 38 via the electronic bus 46 and the bus controller 44. In one embodiment of the invention, the physiological transducing device includes the electronic scale 18. The electronic scale 18 is generally well known and commercially available. The electronic scale 18 may include one or more of the following elements: load cells, pressure transducers, linear variable differential transformers (LVDTs), capacitance coupled sensors, strain gages and semiconductor strain gages. These devices convert the patient's weight into a useable electronic signal that is representative of the patient's weight.

In will be appreciated that Analog-to-Digital (AID) converters are also generally well known and commercially available in a variety of configurations. Furthermore, an A/D converter 15 may be included within the physiological transducing device or within the microprocessor system 24 or within the housing 14. One skilled in the art would have a variety of design choices in interfacing a transducing device comprising an electronic sensor or transducer with the microprocessor system 24.

The scale 18 may provide an analog or digital electronic signal output depending on the particular type chosen. If the electronic scale 18 provides an analog output signal in response to a weight input, the analog signal is converted to a digital signal via the A/D converter 15. The digital signal is then interfaced with the electronic bus 46 and the CPU 38. If the electronic scale 18 provides a digital output signal in response to a weight input, the digital signal may be interfaced with electronic bus 46 and the CPU 38.

Figure 5:
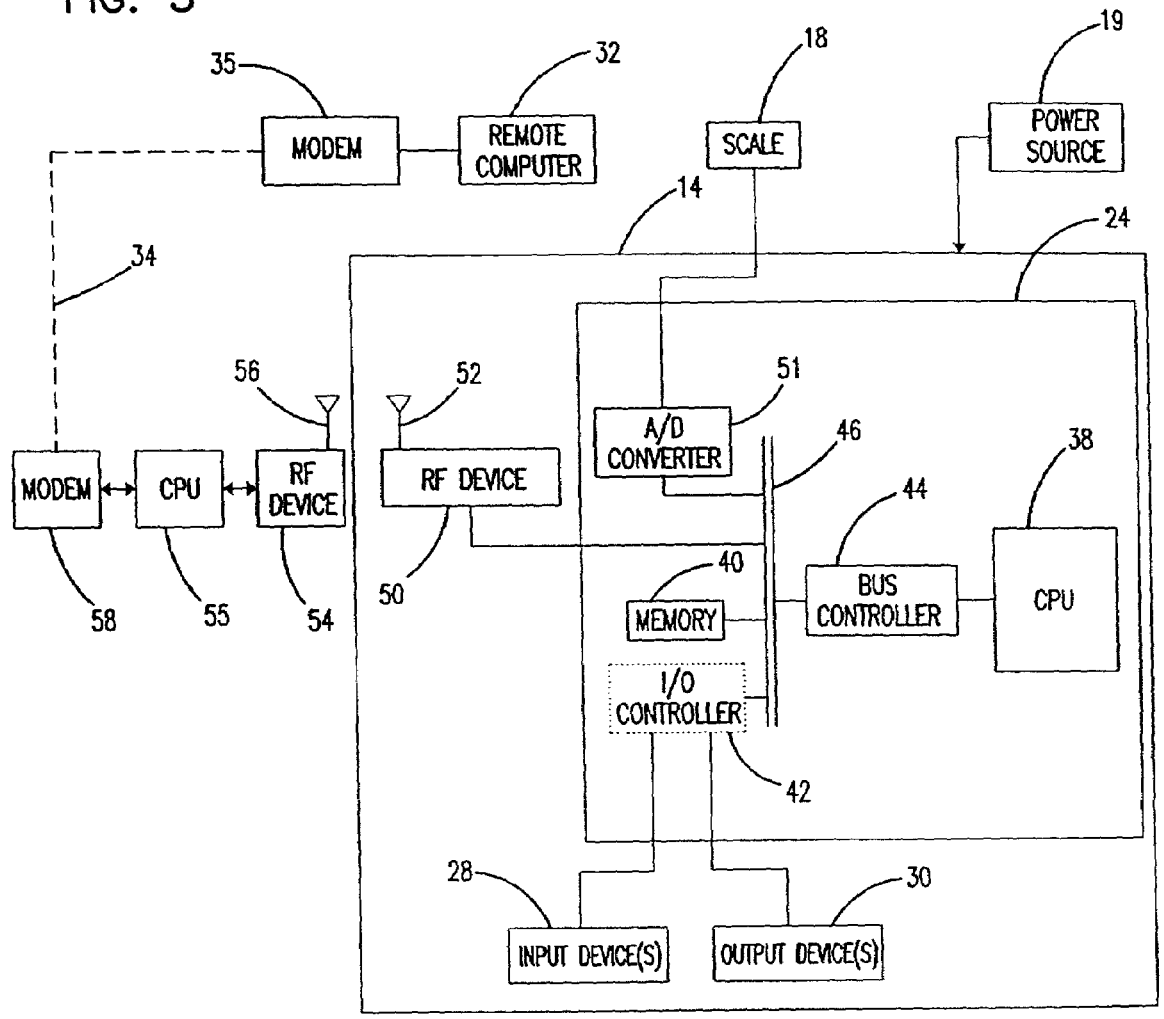
FIG. 5 is functional block diagram of a microprocessor system forming the environment in which one embodiment of the invention may be employed.

FIG. 5 illustrates one embodiment of the invention where the communication device is a radio frequency (RF) transceiver. The transceiver comprises a first radio frequency device 50 including an antenna 52, and a second radio frequency device 54, including an antenna 56. The first radio frequency device 52 is operatively coupled to the microprocessor system 24 via the electronic bus 46, and is in radio communication with the second radio frequency device 54. The second radio frequency device 54 is operatively coupled through a microprocessor 55 which is operatively coupled to a modem 58. The modem 58 is coupled to the communication network 34 and is in communication with the remote computer 32 via the modem 35. The first radio frequency device 50 and the second radio frequency device 54 are remotely located, one from the other. It will be appreciated that such radio frequency devices 50, 54 are generally well known and are commercially available products from RF Monolithics Inc. (RFM).

In one embodiment of the invention, such transceivers operate at radio frequencies in the range of 900-2400 MHz. Information from the microprocessor system 24 is encoded and modulated by the first RF device 50 for subsequent transmission to the second RF device 54, located remotely therefrom. The second RF device 54 is coupled to a conventional modem 58 via the microprocessor 55. The modem 58 is coupled to the communication network 34 via a in-house wiring connection and ultimately to the modem 35 coupled to the remote computer 32. Accordingly, information may be transmitted to and from the microprocessor system 24 via the RF devices 50, 54 via a radio wave or radio frequency link, thus providing added portability and flexibility to the monitoring apparatus 10. It will be appreciated that various other communications devices may be utilized such as RS-232 serial communication connections, Internet communications connection as well as satellite communication connections. Other communications devices that operate by transmitting and receiving infra-red (IR) energy can be utilized to provide a wireless communication link between the patient monitoring apparatus 10 and a conveniently located network connection. Furthermore, X-10™ type devices can also be used as part of a communication link between the patient monitoring apparatus 10 and a convenient network connection in the home. X-10 USA and other companies manufacture a variety of devices that transmit/receive data without the need for any special wiring. The devices works by sending signals through the home's regular electrical wires using what is called power line carrier (PLC).

Figure 6:
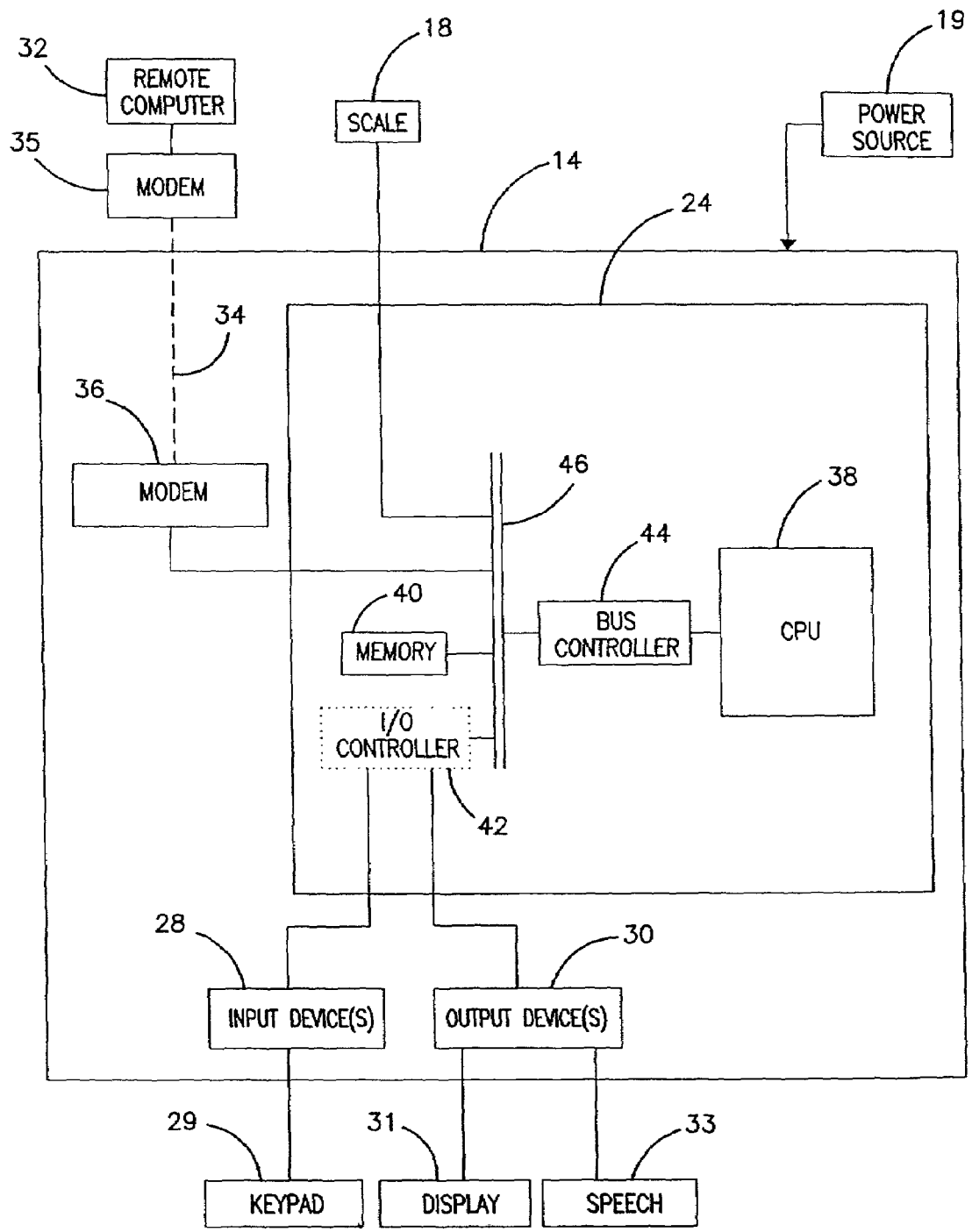
FIG. 6 is a functional block diagram of a microprocessor system forming the environment in which one embodiment of the invention may be employed.

Referring now to FIG. 6, one embodiment of the invention wherein a digital electronic scale 21 is provided. Digital weight measurements from the digital electronic scale 21 may be interfaced with the microprocessor system and CPU 38 without requiring additional amplification, signal conditioning and A/D converters.

Figure 7:
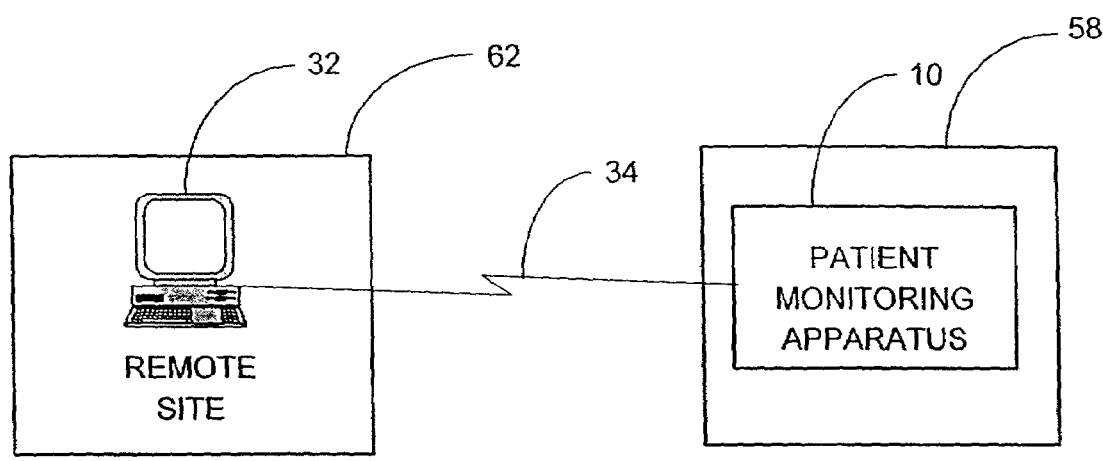
FIG. 7 illustrates a system in which one embodiment of the invention may be employed.

Referring now to FIG. 7, a two way communication system in accordance with the principals of the present invention is shown. The physiological data of an ambulatory patient is monitored utilizing monitoring apparatus 10 at a local site 58 and is transmitted to a remote computer 32 located at a remote computer site 62 via communication network 34. At the remote computer site 62 a medical professional caregiver such as a nurse, physician or nurse practitioner monitors the patient data and provokes treatment in accordance with such data.

Figure 8:
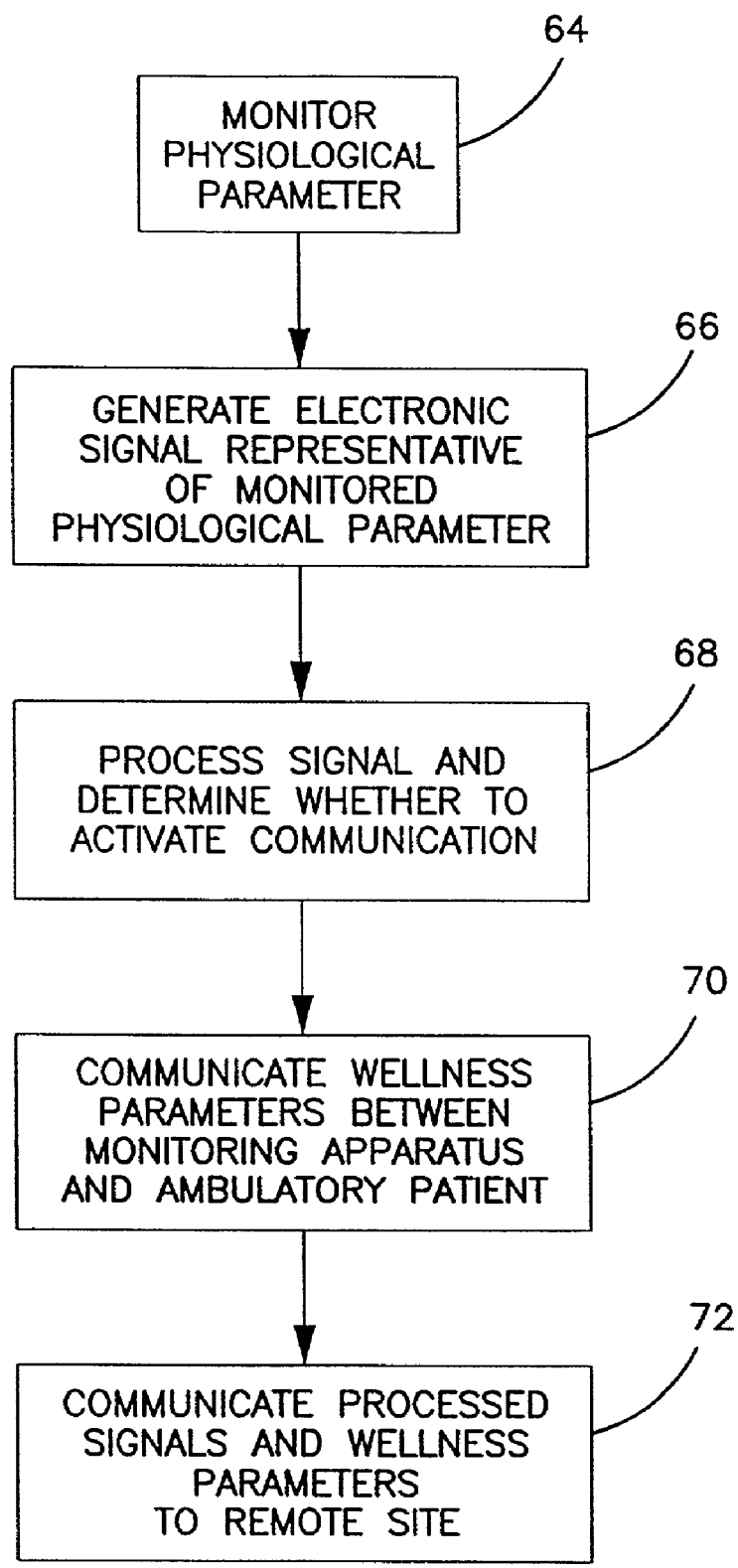
FIG. 8 is a logic flow diagram illustrating the steps utilized to implement one embodiment of the invention.

Operations to perform the preferred embodiment of the invention are shown in FIG. 8. Block 64 illustrates the operation of monitoring or measuring the ambulatory patient's physiological parameter. In one embodiment of the invention, namely for chronic heart failure patients, the physiological parameter monitored is the patient's weight. However, it will be appreciated by those skilled in the art that the physiological parameters may include blood pressure, EKG, temperature, urine output and any other.

Block 66 illustrates the operation of converting a monitored or measured physiological parameter from a mechanical input to an electronic output by utilizing a transducing device. In one embodiment of the invention the transducing device is an electronic scale 18, which converts the patient's weight into a useable electronic signal.

At block 68, the microprocessor system 24 processes the electronic signal representative of the transduced physiological parameter. If the resulting parameter value is within certain preprogrammed limits the microprocessor system 24 initiates communication within the remote computer 32 via the communication device 36 over the communication network 34.

Block 70 illustrates the operation whereby information such as wellness parameters and physiological data are communicated between the monitoring apparatus 10 and the ambulatory patient. An exemplary list of the questions asked to the patient by the monitoring apparatus are provided in Table 5.

Referring now to FIGS. 7 and 8, upon establishing communication between the local monitoring apparatus 10, at the local site 58, and the remote computer 32, at remote site 62, block 72 illustrates the operation of communicating or transmitting processed signals representative of physiological data and wellness parameters from the local site 58 to the remote site 62.

Figure 9:
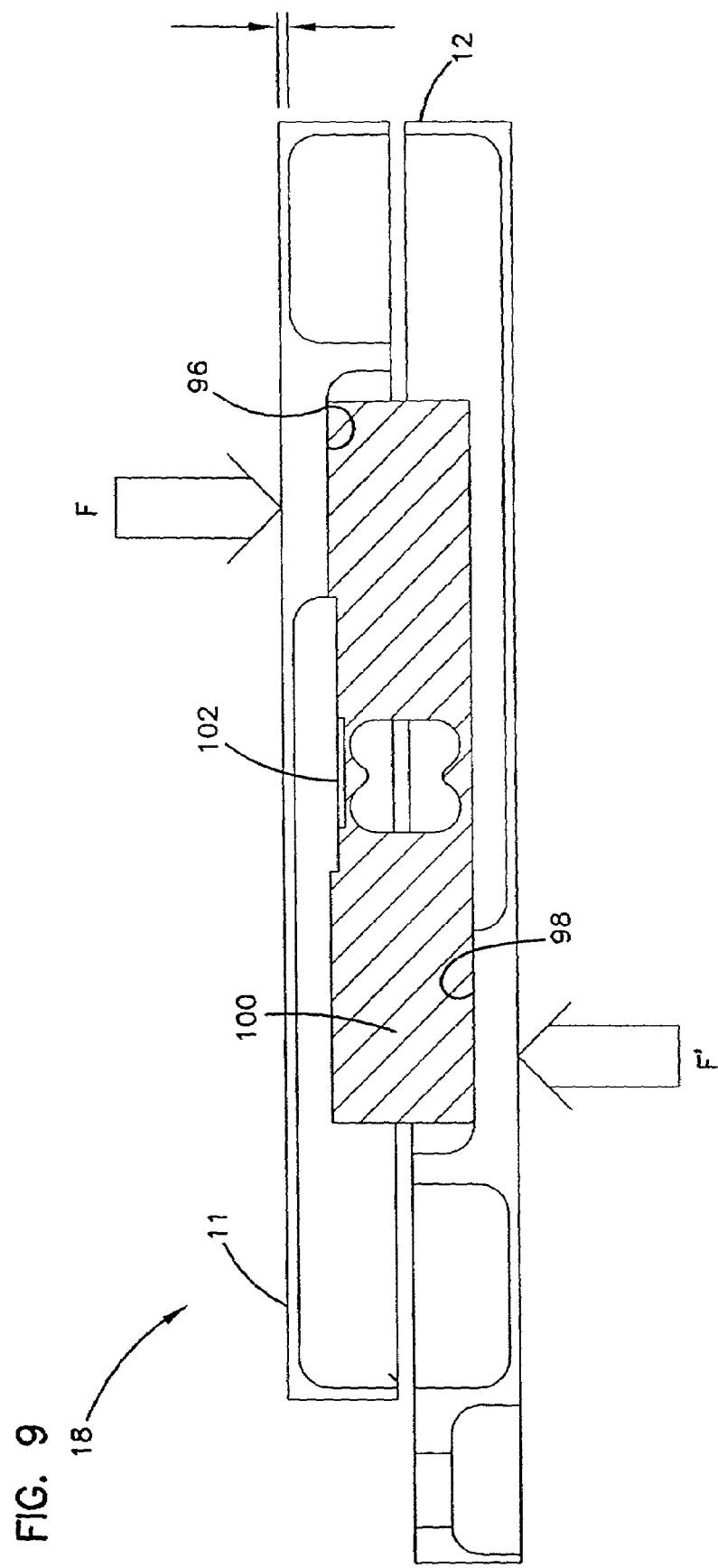
FIG. 9 illustrates a sectional view of the electronic scale in accordance with one embodiment of the invention.

FIG. 9 is a sectional view the scale 18 portion of one embodiment of the invention. The scale 18 comprises a top plate 11 and a base plate 12. The top plate 11 and the base plate 12 having a thickness "T". A load cell 100 is disposed between the top plate 11 and the base plate 12 and rests on support/mounting surfaces 96 and 98.

The load cell 100 is a transducer that responds to a forces applied to it. During operation, when a patient steps on the electronic scale 18, the load cell 100 responds to a force "F" transmitted through the top plate 11 and a first support/mounting surface 96. The support/mounting surface 96 is contact with a first end on a top side of the load cell 100. A force "F'" that is equal and opposite to "F" is transmitted from the surface that the electronic scale 18 is resting on, thorough the base plate 12 and a second support/mounting surface 98. The second support/mounting surface 98 is in contact with a second end on a bottom side of the load cell 100. In one embodiment, the load cell 100 is attached to the top plate 11 and the base plate 12, respectively, with bolts that engage threaded holes provided in the load cell 100. In one embodiment the load cell 100 further comprises a strain gage 102.

The strain gage 102 made from ultra-thin heat-treated metallic foils. The strain gage 102 changes electrical resistance when it is stressed, e.g. placed in tension or compression. The strain gage 102 is mounted or cemented to the load cell 100 using generally known techniques in the art, for example with specially formulated adhesives, urethanes, epoxies or rubber latex. The positioning of the strain gage 102 will generally have some measurable effect on overall performance of the load cell 100. Furthermore, it will be appreciated by those skilled in the art that additional reference strain gages may be disposed on the load cell where they will not be subjected to stresses or loads for purposes of temperature compensating the strain gage 102 under load. During operation over varying ambient temperatures, signals from the reference strain gages may be added or subtracted to the measurement signal of the strain gage 102 under load to compensate for any adverse effects of ambient temperature on the accuracy of the strain gage 102.

The forces, "F" and "F'", apply stress to the surface on which the strain gage 102 is attached. The weight of the patient applies a load on the top plate 11. Under the load the strain gage(s) 102 mounted to the top of the load cell 100 will be in tension/compression as the load cell bends. As the strain gage 102 is stretched or compressed its resistance changes proportionally to the applied load. The strain gage 102 is electrically connected such that when an input voltage or current is applied to the strain gage 102, an output current or voltage signal is generated which is proportional to the force applied to the load cell 100. This output signal is is then converted to a digital signal by A/D converter 15.

Figure 10:
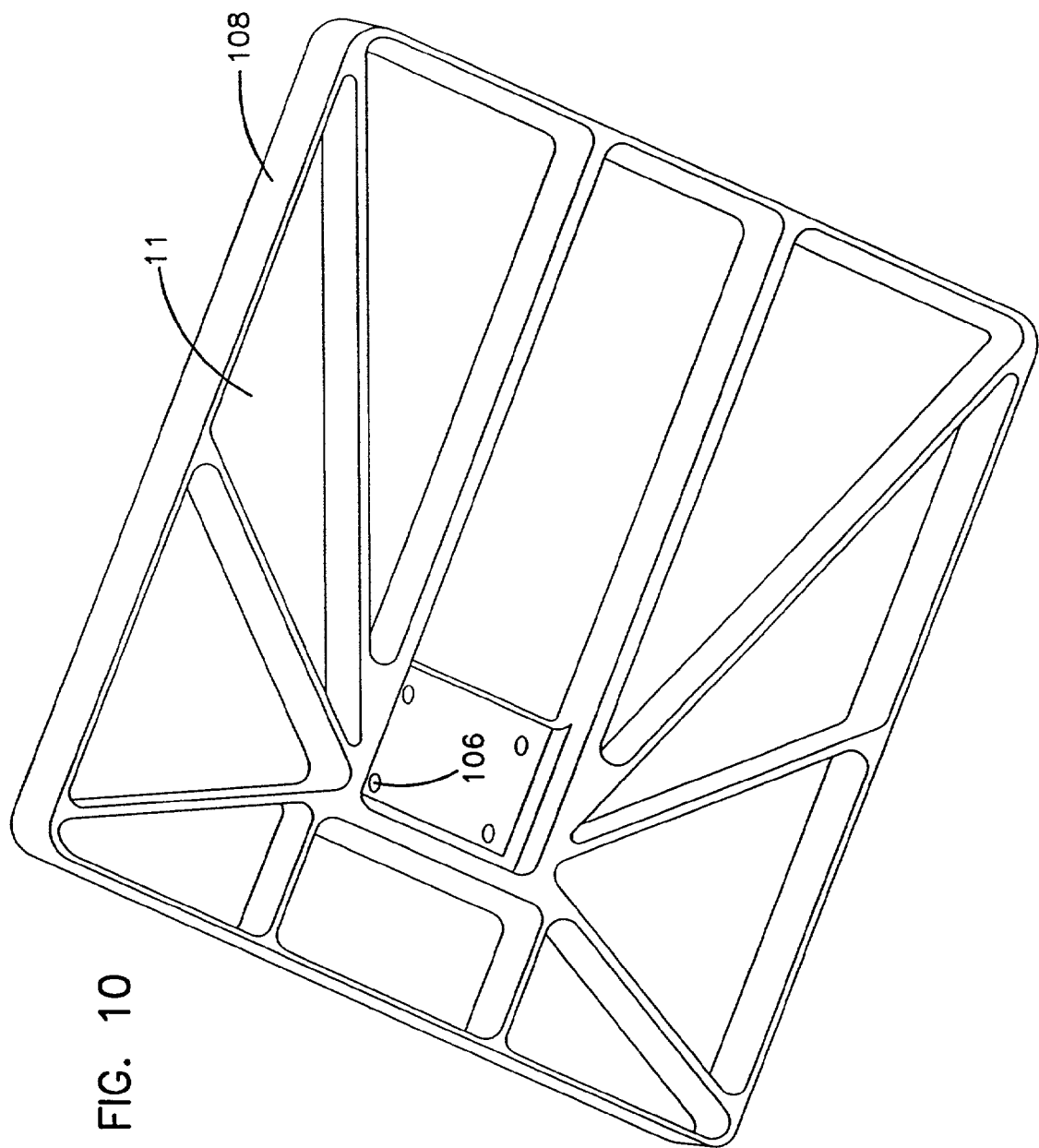
FIG. 10 illustrates a top plate of the electronic scale in accordance with one embodiment of the invention.

The design of the load cell 100 having a first end on a top side attached to the top plate 11 and a second end on a bottom side attached to the base plate 12 provides a structure for stressing the strain gage 102 in a repeatable manner. The structure enables a more accurate and repeatable weight measurement. This weight measurement is repeatable whether the scale 18 rests on a rigid tile floor or on a carpeted floor. FIG. 10 illustrates one embodiment of the top plate 111 that provides four mounting holes 106 for attaching the base plate 12 to one end of the load cell 100. The base plate 12 provides similar holes for attaching to the other end of the load cell 100. The top plate 11 and the base plate 12 (not shown) each comprise a plurality of stiffening ribs 108 that add strength and rigidity to the electronic scale 18.

Table 1 shows multiple comparative weight measurements taken with the electronic scale 18 resting on a tile floor and a carpeted floor without rubber feet on the scale 18. The measurements were taken using the same load cell 100. The thickness "T" of the top plate 11 and supporting ribs was 0.125" except around the load cell, where the thickness of the supporting ribs was 0.250". The thickness of the load cell 100 support/mounting surfaces 96, 98 (FIG. 9) was 0.375". As indicated in Table 1, with the scale 18 resting on a tile floor, the average measured weight was 146.77 lbs., with a standard deviation of 0.11595. Subsequently, with the scale 18 resting on a 0.5" carpet with 0.38" pad underneath and an additional 0.5" rug on top of the carpet, the average measured weight was 146.72 lbs., with a standard deviation of 0.16866.

TABLE 1

Thick Scale Parts Around Load Cell 0.250"

| TILE (lbs.) | CARPET (lbs.) |
|---|---|
| 146.9 | 146.7 |
| 146.7 | 147 |
| 146.9 | 146.6 |
| 146.8 | 146.7 |
| 146.6 | 146.6 |
| 146.8 | 147 |
| 146.8 | 146.5 |
| 146.7 | 146.6 |
| 146.9 | 146.8 |
| 146.6 | 146.7 |
| 0.11595 (stddev) | 0.16866 (stddev) |
| 146.77 (average) | 146.72 (average) |

Table 2 shows multiple weight measurements taken with the scale 18 on a tile floor and a carpeted floor with rubber feet on the bottom of the scale 18. The measurements were taken using the same load cell 100. The thickness "T" of the top plate 11 was 0.125" including the thickness around the load cell. As indicated in Table 2, with the scale 18 resting on a tile floor on rubber feet, the average measured weight was 146.62 lbs., with a standard deviation of 0.07888. Subsequently, with the scale 18 resting on a 0.5" carpet with 0.38" pad underneath and an additional 0.5" rug on top of the carpet, the average measured weight was 146.62 lbs., with a standard deviation of 0.04216.

TABLE 2

Thin Scale Parts Throughout 0.125"

| TILE (lbs.) | CARPET (lbs.) |
|---|---|
| 146.7 | 146.7 |
| 146.7 | 146.7 |
| 146.6 | 146.6 |
| 146.6 | 146.6 |
| 146.6 | 146.6 |
| 146.6 | 146.6 |
| 146.5 | 146.6 |
| 146.7 | 146.6 |
| 146.5 | 146.6 |
| 146.7 | 146.6 |
| 0.07888 (stddev) | 0.04216 (stddev) |
| 146.62 (average) | 146.62 (average) |

Table 3 shows multiple weight measurements taken with an off-the-shelf conventional electronic scale. As indicated in table 3, with the off-the-shelf conventional scale resting on the tile floor, the average measured weight was 165.5571 lbs., with a standard deviation of 0.20702. Subsequently, with the off-the-shelf conventional scale resting on a 0.5" carpet with 0.38" pad underneath and an additional 0.5" rug on top of the carpet, the average measured weight was 163.5143 lbs., with a standard deviation of 0.13093.

TABLE 3

Off-The-Shelf Conventional Scale

| TILE (lbs.) | CARPET (lbs.) |
|---|---|
| 165.9 | 163.5 |
| 165.5 | 163.4 |
| 165.8 | 163.7 |
| 165.4 | 163.6 |
| 165.5 | 163.6 |
| 165.4 | 163.5 |
| 165.4 | 163.3 |

TABLE 3-continued

Off-The-Shelf Conventional Scale

| TILE (lbs.) | CARPET (lbs.) |
|---|---|
| — | 163.4 |
| 0.20702 (stddev) | 0.13093 (stddev) |
| 165.5571 (average) | 163.5143 (average) |
| 2.042857 (% of difference) | 1.249345 (% of difference) |

The summary in Table 4 is a comparative illustration of the relative repeatability of each scale while resting either on a tile floor or on a carpeted floor.

TABLE 4

SUMMARY OF DATA:
Heavy Scale Parts All 0.125" Except Cell
Around the Load Cell 0.250"

| TRIAL | TILE | STDDEV | CARPET | STDDEV | TILE VS. CARPET |
|---|---|---|---|---|---|
| 1 | 146.77 | 0.1159 | 146.72 | 0.1686 | 0.05 |
| 2 | 146.67 | 0.0823 | 146.72 | 0.1906 | 0.05 |
| Thin Scale Parts All 0.125" | | | | | |
| 1 | 146.62 | 0.0788 | 146.62 | 0.04216 | 0.00 |
| Off-The-Shelf Conventional Scale | | | | | |
| 1 | 165.55 | 0.207 | 163.51 | 0.1309 | 2.04 |

The foregoing description was intended to provide a general description of the overall structure of several embodiments of the invention, along with a brief discussion of the specific components of these embodiments of the invention. In operating the apparatus 10, an ambulatory patient utilizes the monitoring apparatus 10 to obtain a measurement of a particular physiological parameter. For example, an ambulatory patient suffering from chronic heart failure will generally be required to monitor his or her weight as part of in-home patient managing system. Accordingly, the patient measures his or her weight by stepping onto the electronic scale 18, integrally located within the base plate 12 of the monitoring apparatus 10.

Referring now to FIG. 4, the modem 36 of the monitoring apparatus 10 will only activate if the measured weight is within a defined range such as +/−10 lbs, +/−10% or any selected predetermined value of a previous weight measurement. The patient's previous symptom free weight (dry weight) is stored in the memory 40. The dry weight is the patient's weight whenever diuretics are properly adjusted for the patient, for example. This prevents false activation of the modem 36 if a child, pet, or other person accidentally steps onto the electronic scale 18.

Upon measuring the weight, the microprocessor system 24 determines whether it is within a defined, required range such as +/−10 lbs. or +/−10% of a previously recorded weight stored in memory 40. The monitoring apparatus 10 then initiates a call via the modem 36 to the remote site 62. Communications is established between the local monitoring apparatus 10 and the remote computer 32. In one embodiment of the invention, the patient's weight is electronically transferred from the monitoring apparatus 10 at the local site 58 to the remote computer 32 at the remote site 62. At the remote site 62 the computer program compares the patient's weight with the dry weight and wellness information and updates various user screens. The program can also analyze the patient's weight trend over the previous 1-21 days. If significant symptoms and/or excessive weight changes are reported, the system alerts the medical care provider who may provoke a change to the patient's medication dosage, or establish further communication with the patient such as placing a telephone to the patient. The communication between the patient's location and the remote location may be one way or two way communication depending on the particular situation.

To establish the patient's overall condition, the patient is prompted via the output device(s) 30 to answer questions regarding various wellness parameters. An exemplary list of questions, symptoms monitored and the related numerical score is provided in Table 5 as follows:

TABLE 5

Health Check Score

| Question | Symptom | Value |
| --- | --- | --- |
| Above Dry Weight? | Fluid accumulation | 10 |
| Are you feeling short of breath? | Dyspnea | 10 |
| Did you awaken during the night short of breath? | Paroxysmal nocturnal dyspnea | 5 |
| Did you need extra pillows last night? | Congestion in the lungs | 5 |
| Are you coughing more than usual? | Congestion in the lungs | 3 |
| Are your ankles or feet swollen? | Pedal edema | 5 |
| Does your stomach feel bloated? | Stomach edema | 3 |
| Do you feel dizzy or lightheaded? | Hypotension | 5 |
| Are you more tired than usual? | Fatigue | 2 |
| Are you taking your medication? | Medication compliance | 7 |
| Has your appetite decreased? | Appetite | 2 |
| Are you reducing your salt intake? | Sodium intake | 1 |
| Did you exercise today? | Fitness | 1 |

At the remote site 62 the medical professional caregiver evaluates the overall score according to the wellness parameter interrogation responses (as shown in Table 5). For example, if the patient's total score is equal to or greater than 10, an exception is issued and will either prompt an intervention by the medical professional caregiver in administering medication, or prompt taking further action in the medical care of the patient.

The output device(s) 30 varies based on the embodiment of the invention. For example, the output device may be a synthetic speech generator 33. As such, the wellness parameters are communicated to the patient via the electronic synthetic speech generator 33 in the form of audible speech. It will be appreciated that electronic speech synthesizers are generally well known and widely available. The speech synthesizer converts electronic data to an understandable audible speech. Accordingly, the patient responds by entering either "YES" or "NO" responses into the input device 28, which may include for example, an electronic keypad 29. However, in one embodiment of the invention, the input device may also include a generic speech recognition device such as those made by International Business Machines (IBM), Dragon Systems, Inc. and other providers. Accordingly, the patient replies to the interrogations merely by speaking either "YES" or "NO" responses into the speech recognition input device.

In embodiments of the invention that include electronic display 31 as an output device 30, the interrogations as well as the responses are displayed and/or scrolled across the display for the patient to read. Generally, the electronic display will be positioned such that it is viewable by the patient during the information exchanging process between the patient and the remote computer 32.

Upon uploading the information to the remote computer 32, the medical professional caregiver may telephone the patient to discuss, clarify or validate any particular wellness parameter or physiological data point. Furthermore, the medical professional caregiver may update the list of wellness parameter questions listed in Table 5 from the remote site 62 over the two way communication network 34. Modifications are transmitted from the remote computer 32 via modem 35, over the communication network 34, through modem 36 and to the monitoring apparatus 10. The modified query list is then stored in the memory 40 of the microprocessor system 24.

Two-Way Communication

Figure 11:
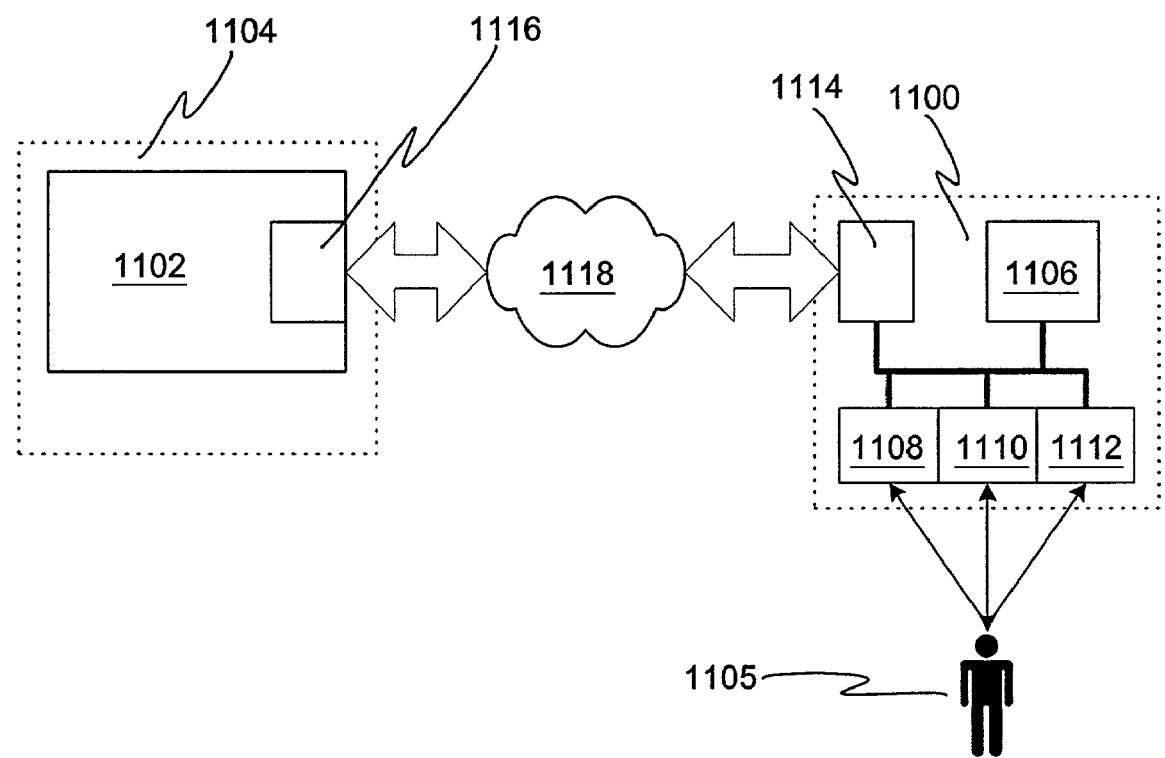
FIG. 11 illustrates a high-level depiction of a monitoring system utilizing two-way communication, in accordance with one embodiment of the present invention.

FIG. 11 is presented in furtherance of the previous discussion regarding two-way communication between the patient monitoring apparatus and the central computer. FIG. 11 is a high-level depiction of the monitoring system, and may be used as a starting point for a more detailed discussion of the two-way communication schemes.

As can be seen from FIG. 11, the system comprises a patient monitoring apparatus 1100 and a central computer 1102. The central computer 1102 is housed within a facility 1104 that is located remote from the patient monitoring apparatus 1100. For example, the patient monitoring apparatus 1100 may be located in the home of an ambulatory patient 1105, while the central computer 1102 is located in a cardiac care facility 1104.

As described previously, the patient monitoring apparatus 1100 is composed of a central processor unit 1106, which is in communication with an input device 1108, an output device 1110, and a sensor 1112. As also previously described the sensor 1112 may be a transducer used to convert a physiological measurement into a signal, such as an electrical signal or an optical signal. For example, the sensor 1112 may comprise a load cell configured with a strain gauge, arranged to determine the patient's 1105 weight; the sensor 1112 would represent the patient's 1105 weight as an electrical signal.

As discussed previously, the output device 1110 may be used to prompt the patient 1105 with questions regarding the patient's wellness. The output device 1110 may consist of a visual display unit that displays the questions in a language of the patient's 1105 choosing. Alternatively, the output device 1110 may consist of an audio output unit that vocalizes the questions. In one embodiment, the audio output unit 1110 may vocalize the questions in a language of the patient's 1105 choosing.

As discussed previously, the input device 1108 may be used to receive the patient's 1105 response to the questions posed to him/her 1105. The input device 1108 may consist of a keyboard/keypad, a set of buttons (such as a "yes" button and a "no" button), a touch-screen, a mouse, a voice digitization package, or a voice recognition package.

The patient monitoring apparatus 1100 communicates with the central computer 1102 via a network 1118; the patient monitoring apparatus 1100 uses a communication device 1114 to modulate/demodulate a carrier signal for transmission via the network 1118, while the central computer uses a communication device 1116 for the same purpose. Examples of suitable communication devices 1114 and 1116 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network.

A system composed as described above may be programmed to permit two-way communication between the central computer 1102 and the patient monitoring apparatus

1100. Two-way communication may permit the central computer 1102 to upload a customized set of questions or messages for presentation to a patient 1105 via the monitoring apparatus 1100. For example, in the case where the monitoring apparatus 1100 monitors the patient's 1105 weight, a sudden increase in weight following a high sodium meal might cause the health care provider to send a customized question for presentation to the patient 1105: "Did consume any salty food in the last 24 hours?" Such a customized question could be presented to the patient 1105 the next time the patient uses the monitoring apparatus 1100 or could be presented to the patient in real time (these options are discussed in greater detail, below). Additionally, a customized message may be scheduled for delivery at certain times (such as every Friday of the week—this is also discussed in greater detail, below). Further, these customized messages may be entered on the fly or selected from a list (this is also discussed in greater detail below).

Figure 12:
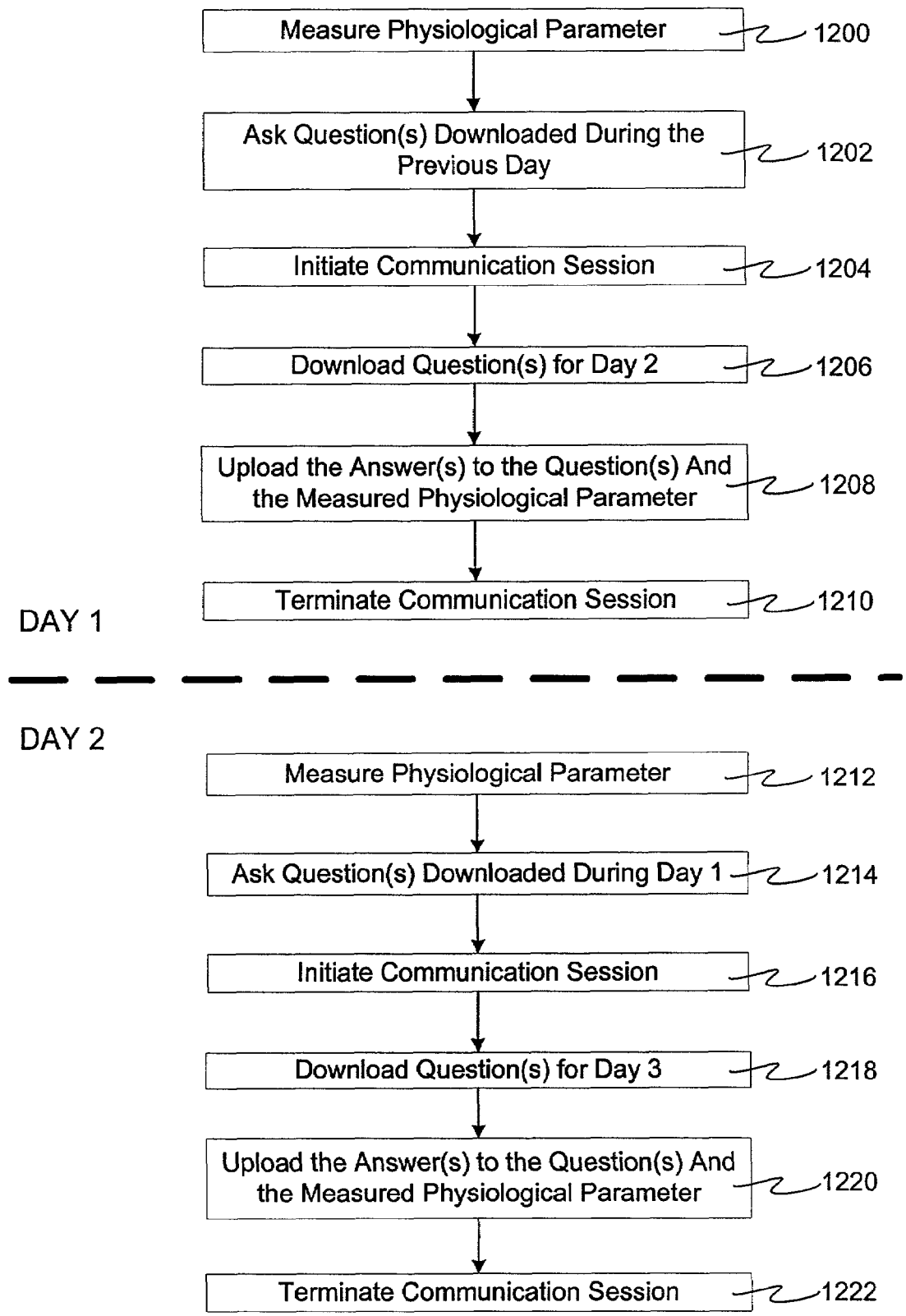
FIG. 12 depicts a flow of operation that permits two-way communication between a central computer and a monitoring apparatus.

FIG. 12 depicts a flow of operations that permits two-way communication between the central computer 1102 and the monitoring apparatus 1100. FIG. 12 presents a flow of interactions between the central computer 1102 and the monitoring apparatus 1100 on a first day (operation 1200-1210) and on a second day (1212-1222). In the discussion that follows, it will be assumed that the monitoring apparatus 1100 is formed as a scale that monitors a patient's weight, although this need not be the case. It is further assumed that the patient 1105 measures his/her weight on a daily basis (although, in principle, any frequency of measurement would operate within the bounds of this embodiment), after which a communication session is initiated between the central computer 1102 and the monitoring apparatus 1100.

On the first day, operation begins with the patient 1105 stepping on the scale, as shown in operation 1200; the patient's 1105 weight is measured, transduced, and stored by the central processing unit 1106. Next, in operation 1202, a memory device is accessed by the central processing unit 1106 for the purpose of retrieving a set of customized questions downloaded during the previous day. Each question is asked, in a one-by-one fashion, and a corresponding answer received from the patient 1105 via the input device 1108 is recorded (if the customized prompt is merely a statement, the statement is output to the patient and no answer is requested of the patient 1105). Next, in operation 1204, a communication session is initiated. The session may be initiated manually (for example, by the patient pushing a button); the session may be initiated automatically by the scale at a specific time of the day (such as at midnight, after the patient 1105 is assumed to have weighted himself/herself and recorded his/her answers to the customized wellness questions); the session may be initiated automatically by the scale upon the patient 1105 answering the final question; finally, the session may be initiated by the central computer 1102 at a specific time of the day (such as at midnight, after the patient 1105 is assumed to have weighted him/herself and recorded his/her answers to the customized wellness questions). During the communication session, customized questions to be asked to the patient 1105 the next day are downloaded by the monitoring apparatus 1100, as depicted in operation 1206. Additionally, the answers recorded in operation 1202 are uploaded to the central computer 1102, as depicted in operation 1208. Finally, in operation 1210, the communication session is terminated.

On the second day, the same set of operations takes place, with references to previous and future days now referring to "DAY 1" and "DAY 3," respectively: in operation 1214, the set of questions downloaded during the first day (in operation 1206) are asked, and the answers are recorded; similarly, in operation 1218, a set of customized questions to be asked on a third day are uploaded to the monitoring apparatus 1100.

Downloading operations (such as operations 1206 and 1218) and uploading operations (such as operation 1208 and 1220) may be influenced by the form of input device 1108 or output device 1110 chosen for use by the monitoring apparatus 1100. For example, if the output device 1110 is a visual display, then a set of data representing the text of the question is transmitted to the monitoring apparatus 1100 during the downloading operations 1206 and 1208. If, however, the output device 1110 is an audio output device, then a set of data representing a vocalization of the question may be transmitted to the monitoring apparatus 1100 during the downloading operations 1206 and 1208. In any case, the data being transmitted to the monitoring apparatus 1100 may be compressed for the sake of preservation of bandwidth. Similar considerations apply to the uploading operations 1208 and 1220, based upon the choice of input device 1108. If the input device 1108 is a set of buttons (for example, a "yes" button and a "no" button), then the data uploaded to the central computer 1102 is representative of the button that was pushed. If the input device 1108 is a voice digitization package, then the data uploaded to the central computer 1102 is representative of the digitized voice pattern from the patient 1105. As in the case of the downloading operations, the data being uploaded to the central computer 1102 may be compressed for the sake of preservation of bandwidth.

Figure 13:
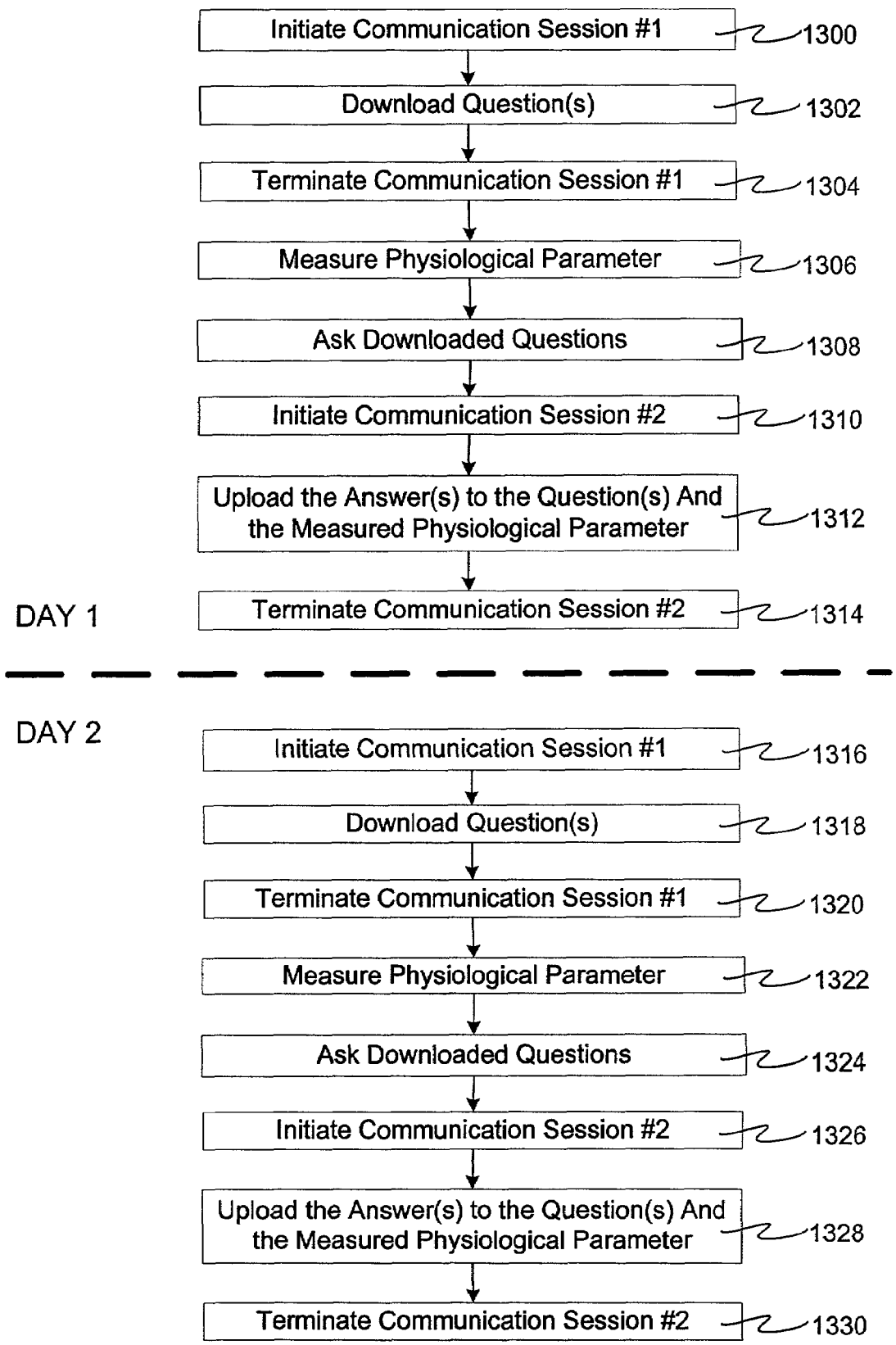
FIG. 13 depicts another flow of operation that permits two-way communication between a central computer and a monitoring apparatus.
Figure 14:
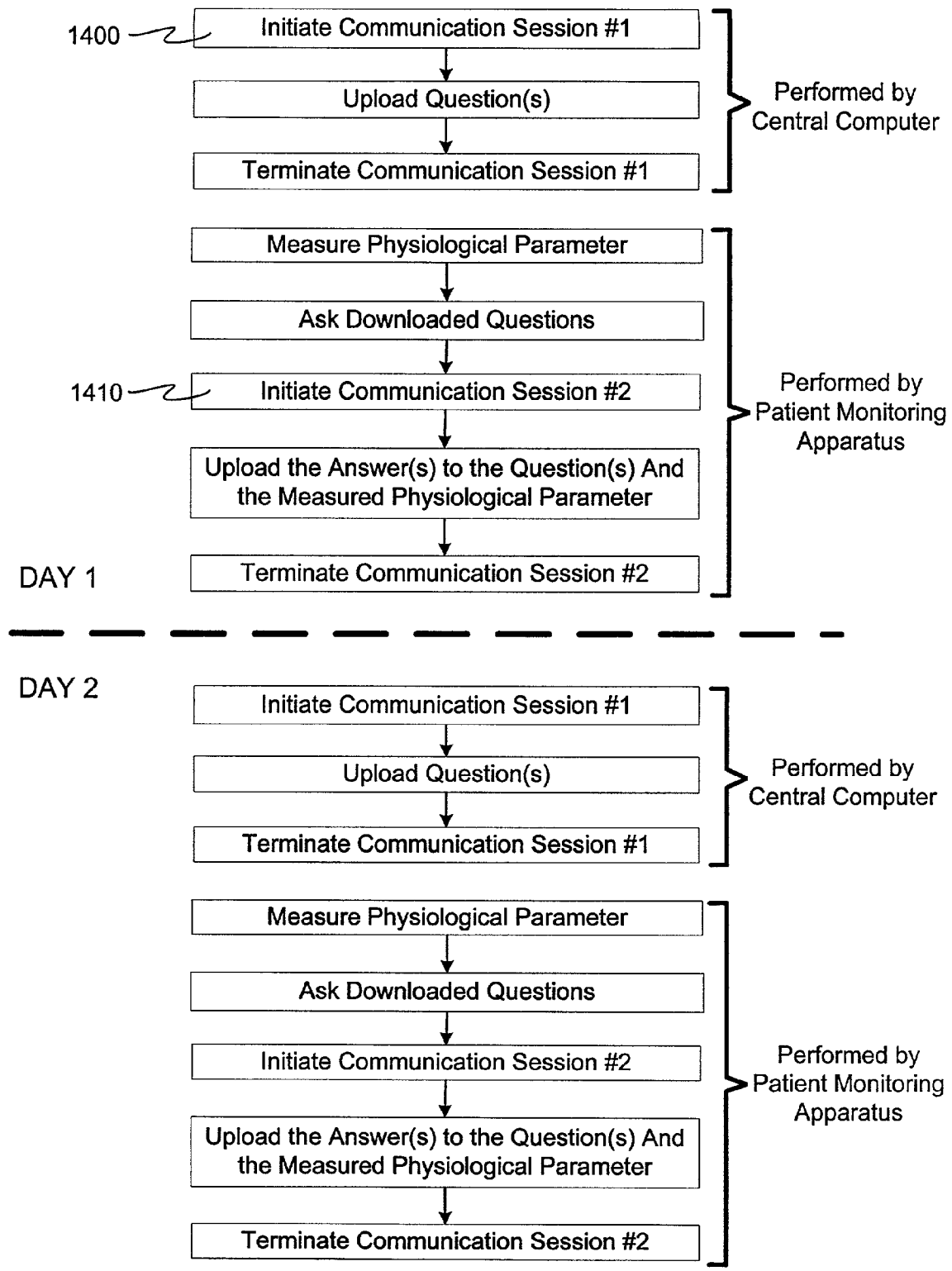
FIG. 14 depicts yet another flow of operation that permits two-way communication between a central computer and a monitoring apparatus.
Figure 15:
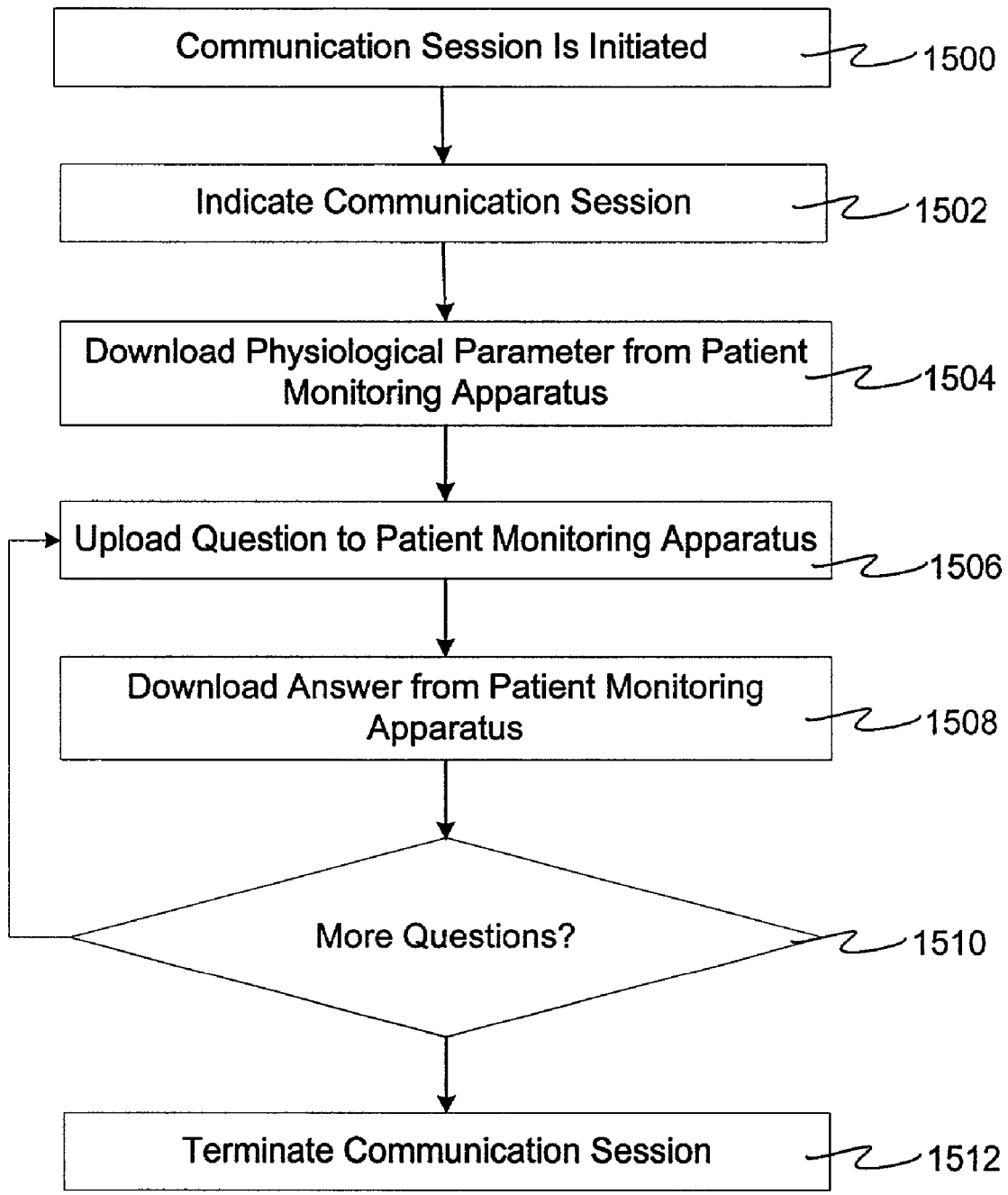
FIG. 15 depicts a flow of operation that permits real-time two-way communication between a central computer and a monitoring apparatus.

FIGS. 13, 14, and 15 depict other flows of operation for two-way communication between a central computer 1102 and a patient monitoring apparatus 1100. The considerations regarding the format of the data being uploaded and downloaded also apply to the schemes illustrated therein.

FIG. 13 depicts a flow of operations that permits two-way communication between the central computer 1102 and the monitoring apparatus 1100. FIG. 13 presents a flow of interactions between the central computer 1102 and the monitoring apparatus 1100 on a first day (operation 1300-1314) and on a second day (1316-1328). In the discussion that follows, it will be assumed that the monitoring apparatus 1100 is formed as a scale that monitors a patient's weight, although this need not be the case. It is further assumed that the patient 1105 measures his/her weight on a daily basis (although, in principle, any frequency of measurement would operate within the bounds of this embodiment).

On the first day, operation begins with a communication session between the central computer 1102 and the monitoring apparatus 1100 being initiated, as shown in operation 1300. During this communication session, a set of customized questions to be asked to the patient 1105 later in the day are downloaded by the monitoring apparatus 1100, as depicted in operation 1302. Then, in operation 1304, the communication session is terminated. The communication session initiated in operation 1300 may be initiated by the monitoring apparatus. Additionally, the session may be initiated at a time of the day that justifies the assumption that any new customized questions would have already been entered for downloading by the monitoring device 1100. At some point in the day after the termination of the communication session, the patient 1105 weighs himself on the monitoring apparatus, as shown in operation 1306, and the weight is stored by the central processor unit 1106. Next, in operation 1308, a memory device is accessed by the central processing unit 1106 for the purpose of retrieving the set of customized questions downloaded earlier in the day during operation 1302. Each question is asked, in a one-by-one fashion, and a corresponding answer received from the patient 1105 via the input device 1108 is recorded. Next, in operation 1310, a communication session is initiated. As in the scheme depicted in FIG. 12, the session may be initiated manually or automatically. During this session, the answers recorded in operation 1308 are uploaded to the central computer 1102, as depicted in operation 1312. Finally, in operation 1314, the communication session is terminated.

As can be seen from FIG. 13, the set of operations performed on the second day (operations 1316-1328) are identical to the operations performed on the first day (operations 1300-1314).

FIG. 14 depicts another flow of operations that permits two-way communication between the central computer 1102 and the monitoring apparatus 1100. The flow of operations depicted in FIG. 14 is the same as that which is shown in FIG. 13, with minor exceptions. The flow depicted in FIG. 14 is arranged such that the central computer 1102 initiates the first communication session (in operation 1400), during which a set of customized questions are downloaded by the monitoring device; however, later in the day, the monitoring device 1100 initiates the second communication session (in operation 1410), during which the patient's 1105 weight and answers to the customized questions are transmitted to the central computer 1102. This scheme has the advantage of allowing the central computer 1102 to initiate the session during which the customized questions are uploaded to the monitoring apparatus 1100, thereby ensuring that the communication session occurs after the new questions have been entered by the health care provider (if the monitoring apparatus 1100 initiates the communication session, as in FIG. 13, the session may be initiated before the new questions are entered). Just as in the scheme depicted in FIG. 13, the scheme depicted in FIG. 14 employs the same set of operations from day to day.

FIG. 15 depicts a flow of operations that permits real-time two-way communication between the central computer 1102 and the monitoring apparatus 1100. In the discussion that follows, it will be assumed that the monitoring apparatus 1100 is formed as a scale that monitors a patient's weight, although this need not be the case. It is further assumed that the patient is free to weight himself/herself at any time during the day and that the measured weight will be stored. The scheme depicted in FIG. 15 permits the patient 1105 to initiate a communication session, during which the health care provider may, via the central computer, enter questions that are posed to the patient in real-time via the monitoring apparatus 1100. The communication session does not end until the health care provider indicates that it has no further questions to ask the patient. Thus, the health care provider may adapt its questions in real-time, based upon the answers received from the patient 1105.

Operation begins with a communication session between the central computer 1102 and the monitoring apparatus 1100 being initiated, as shown in operation 1500. Next, in operation 1502, the central computer 1102 generates a visual cue on its graphical user interface to indicate that a particular patient is logged in. A health care provider/operator at the central computer 1102 is thereby made aware of his/her opportunity to prompt the patient 1105 with customized questions in real-time. Subsequently, in operation 1504, the weight of the patient 1105 is uploaded to the central computer. As mentioned earlier, the patient 1105 is assumed to have weighed himself/heself at a point in the day prior to the initiation of the communication session in operation 1500. This permits the patient 1105 to consistently measure his/her weight at a given point in the day (perhaps immediately upon waking in the morning), yet answer questions regarding his/her symptoms at a point later in the day, so that the patient 1105 has had a chance to judge his/her general feeling of health/illness before answering the questions. Of course, this is an optional feature of the invention and is not crucial. In operation 1506, a first customized question is uploaded to the monitoring apparatus. During operation 1506, a health care provider/operator may enter a question to be posed to the patient 1105; it is immediately transmitted to the monitoring apparatus 1100 and posed to the patient 1105. In operation 1508, the patient's answer is transmitted to the central computer 1102. Next, in operation 1510, the operator/health care provider at the central computer 1102 indicates whether or not any additional questions are pending. If so, control is passed to operation 1506, and the additional questions are asked and answered. Otherwise, the communication session is terminated in operation 1512.

Scheduling of Questions and Presentation of Trending Data

Figure 16:
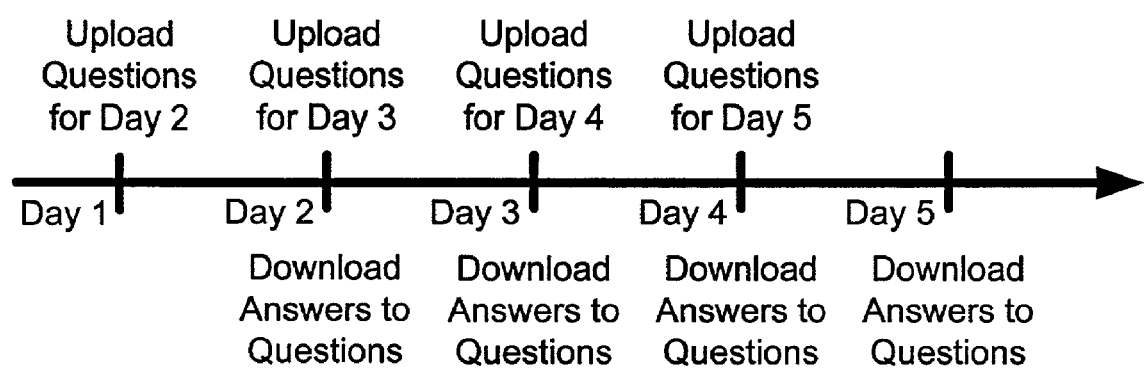
FIG. 16 depicts a scheme of asking customized questions and collecting the answers thereto.

FIG. 16 illustrates a scheme of asking customized questions and collecting the answers thereto. As can be seen from FIG. 16, a set of customized questions may be downloaded to a monitoring device 1100 on DAY N. The customized questions will be asked to the patient 1105, and the answers recorded either later in the day on DAY N or on DAY N+1 (depending upon the particular 2-way scheme employed). The answers to the customized questions are retrieved by the central computer 1102 on DAY N+1. The particular questions asked from day-to-day may vary, based upon instruction from the health care provider.

Figure 17:
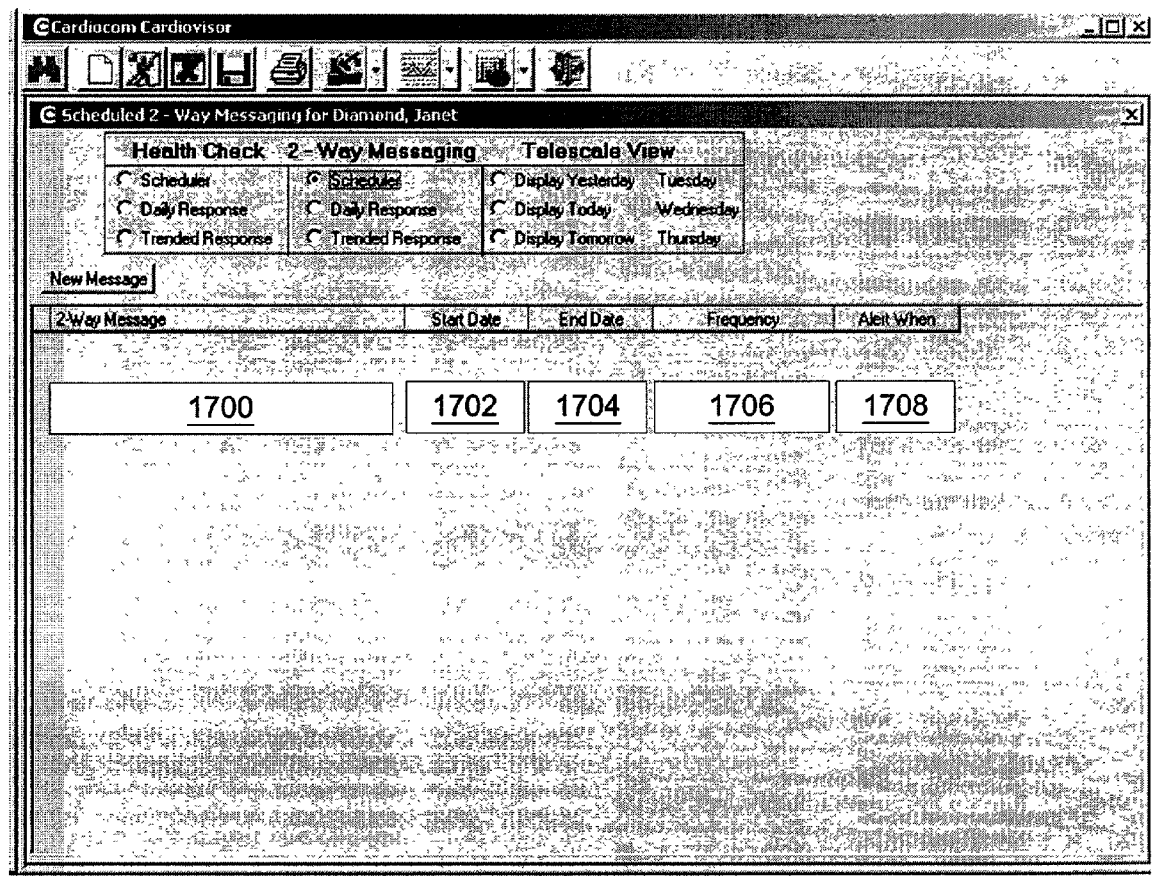
FIG. 17 illustrates a graphical user interface that may be used in conjunction with software running on a central computer for the purpose of scheduling questions to be uploaded each day to a monitoring apparatus for questioning of a patient.

FIG. 17 illustrates a graphical user interface that may be used in conjunction with software running on the central computer 1102 for the purpose of scheduling the questions to be uploaded each day to the monitoring apparatus 1100 (as illustrated by FIG. 16) for questioning of the patient 1105. As can be seen from FIG. 17, a message field 1700 is provided that permits an operator/health care provider to enter a customized message to be uploaded to the monitoring apparatus 1100. A start-date field 1702 and an end-date field 1704 define the period during which the questions are to be asked; a frequency field indicates 1706 the frequency with which the question entered in field 1700 is to be asked. For example, if the message field 1700 contained the question "Did you remember to take your medication this week?", the start-date field 1702 contained "Aug. 1, 2001," the end-date field 1704 contained "Sep. 1, 2001," and the frequency field 1706 contained "Friday," then the patient 1105 would be prompted with the question "Did you remember to take your medication this week?" on each Friday between Aug. 1, 2001 and Sep. 1, 2001. An alert field 1708 permits an operator/health care provider to define an answer that, when provided by patient 1105, sends an alert to the health care provider. For example, in the case where the question was "Did you remember to take your medication this week?", the alert field 1708 may contain the answer "No," so that the health care provider would be alerted if the patient 1105 indicated that he/she had failed to take his/her medication during the week.

The data entered via the graphical user interface depicted in FIG. 17 is stored in a database. The data may be organized based upon dates for transmission to the monitoring device 1100, so that all of the questions to be uploaded to the monitoring device 1100 on a given day may be easily acquired. The data may be sorted other ways, as well. For example, the data may be sorted based upon which questions were asked on which days, so that a presentation of the questions posed to a patient on a given day (or set of days) and the corresponding answers thereto may be easily developed. A graphical user interface that provides such a presentation is depicted in FIG. 18.

Figure 18:
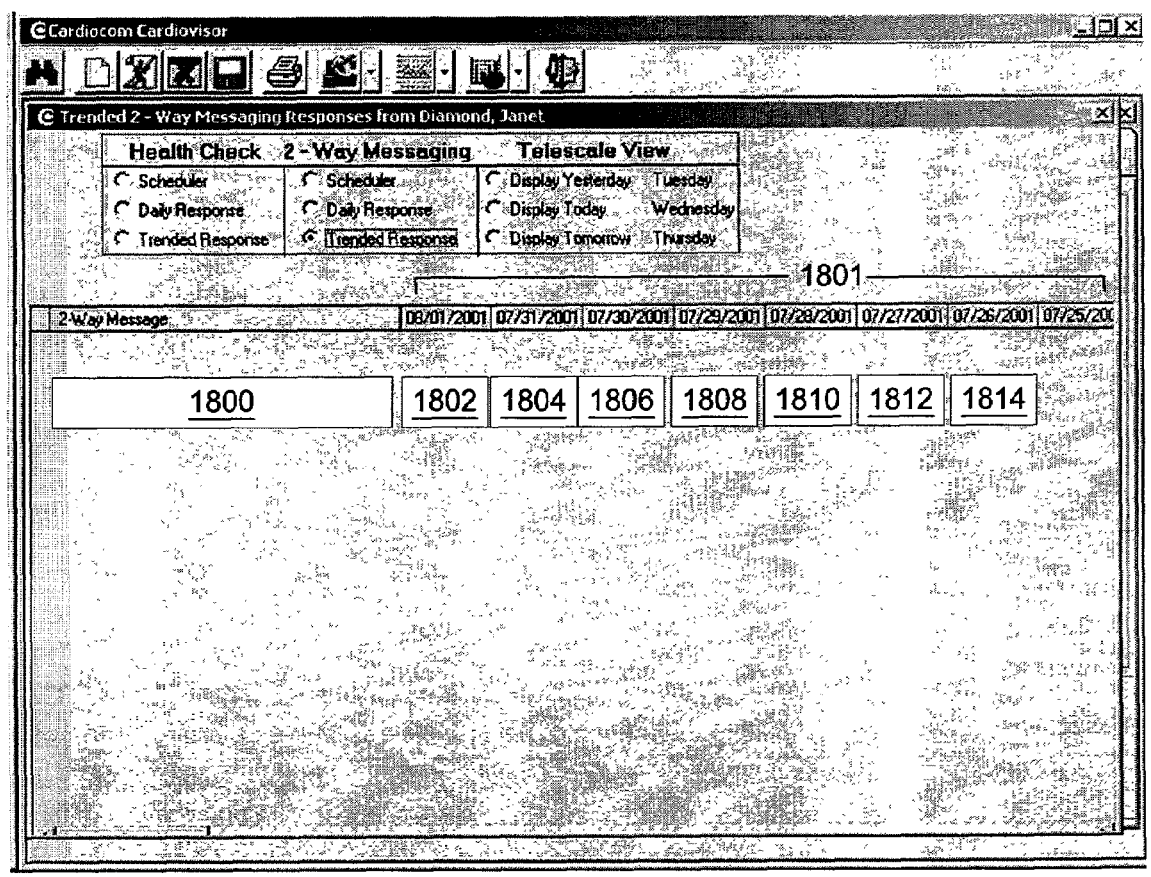
FIG. 18 illustrates a graphical user interface that may be used in conjunction with software running on a central computer for presenting a set of trending data.

FIG. 18 depicts a graphical user interface that presents all of the customized questions presented to a patient over a particular duration and all of the corresponding answers for each day. This sort of information is referred to as "trending data," because it permits a health care provider to quickly determine if a particular symptom began regularly exhibiting itself on a certain day, or if a particular symptom is randomly exhibited. As can be seen from FIG. 18, a message field 1800 is provided which presents a customized question that was asked during the timeframe indicated by the date bar 1801. Under each date presented in the date bar 1801 is an answer field 1802-1816, which presents the patient's 1105 answer to the question presented in the message field 1800. If a particular question was not asked on a given day, the graphical user interface may so indicate. For example, an answer field 1802-1816 may be grayed out on a particular day if the question was not asked, or an answer field may be highlighted on days in which the particular question was asked. As described earlier, the data used to populate fields 1800-1816 is retrieved from a database containing each of the questions asked on a given day and each of the corresponding answers.

Other reporting schemes and graphical user interfaces are taught in U.S. application Ser. No. 09/399,041 filed on Sep. 21, 1999, entitled "MEDICAL WELLNESS PARAMETERS MANAGEMENT SYSTEM, APPARATUS AND METHOD," which is hereby incorporated by reference in its entirety.

Collapsible Scale/Carpet-Spike Pads

Figure 19:
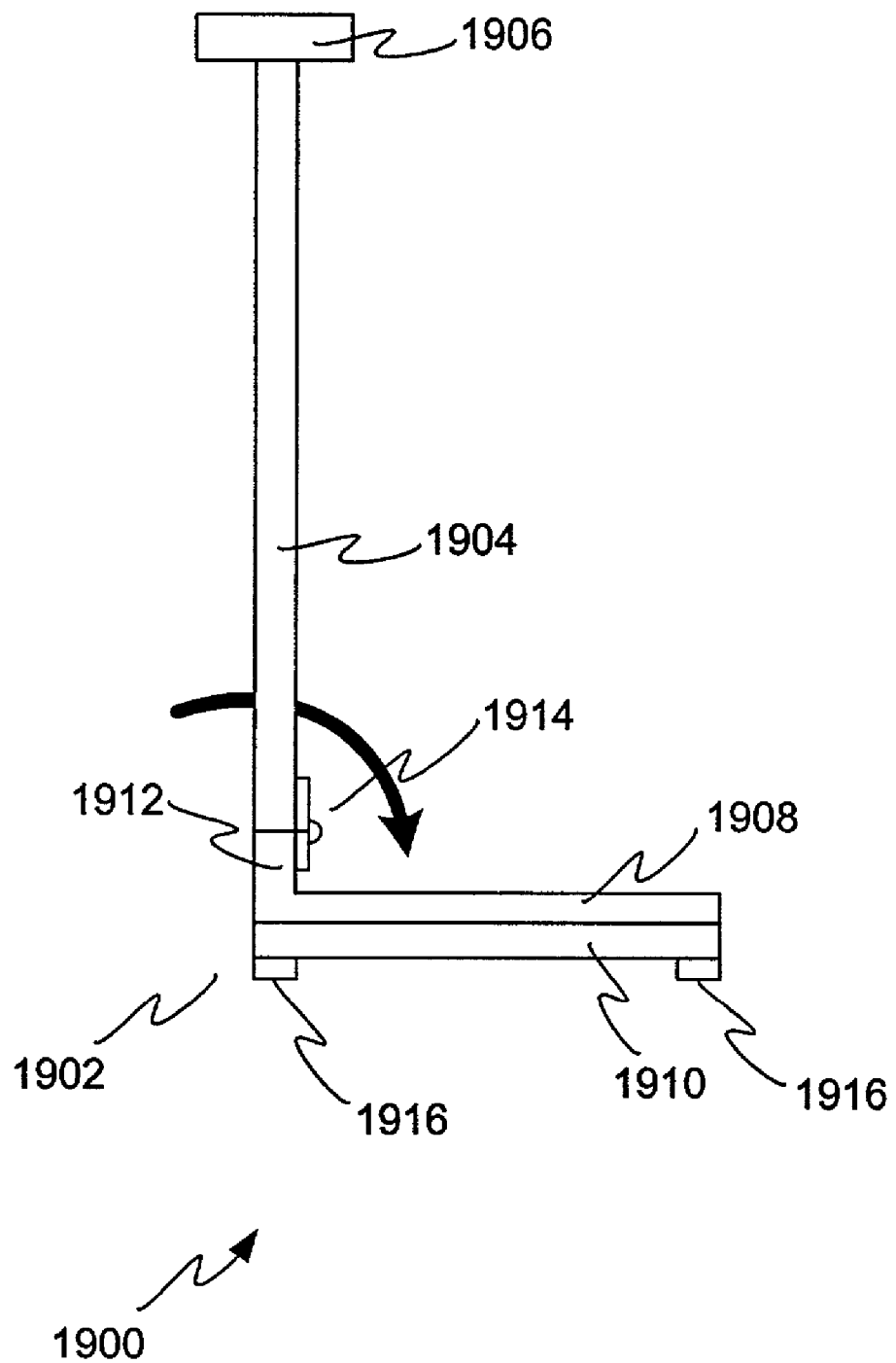
FIG. 19 depicts a collapsible scale with carpet-spike pads, in accordance with one embodiment of the invention.

FIG. 19 depicts a collapsible scale 1900 with integrated carpet-spike pads, in accordance with one embodiment of the present invention. As can be seen from FIG. 19, a collapsible scale 1900 is comprised of a base 1902, upon which a patient 1105 stands in order to weigh himself/herself. Perpendicular to the base 1902 is a support member 1904 which elevates a housing 1906 at about waist level. The housing 1906 may contain an input device, an output device, a processor, and a communication device. The support member 1904 is coupled to the base 1902 via a hinge 1914. The hinge 1914 enables the support member 1904 to fold into a position approximately parallel (though not necessarily coplanar) with the base 1902, thereby permitting the scale 1900 to fit easily (and in one piece) into a box suitable for shipping. Another advantage of the collapsible embodiment is that it relieves the patient 1105 of having to assemble the scale at his/her home.

The base 1902 may be composed of top plate 1908, upon which the patient 1105 stands, and a base plate 1910. The hinge 1914 may be coupled to the support member 1904 and the top plate 1908, so that if the patient leans upon the housing 1906, the force is conducted down the support member 1904, though the hinge 1914, and to the top plate 1908, thereby preserving the validity of the weight measurement. Alternatively, the top plate 1908 may have member 1912 rigidly coupled thereto. In such a case, the hinge 1914 may be coupled between the support member 1904 and the rigidly coupled member 1912.

In one embodiment of the scale 1900, a plurality of carpet-spike pads 1916 are attached to the bottom of the base 1902. A carpet-spike pad 1926 is a disk with a plurality of spikes that protrude downwardly therefrom. The carpet-spike pads 1916 improve the stability of the scale 1900 upon carpet-like surfaces, thereby enhancing the accuracy and repeatability of measurements taken therewith. The carpet-spike pads 1916 may be attached to the base 1902 by an adhesive, by force fit, or may be integrated into the base 1902 itself.

Question Hierarchies

Figure 20:
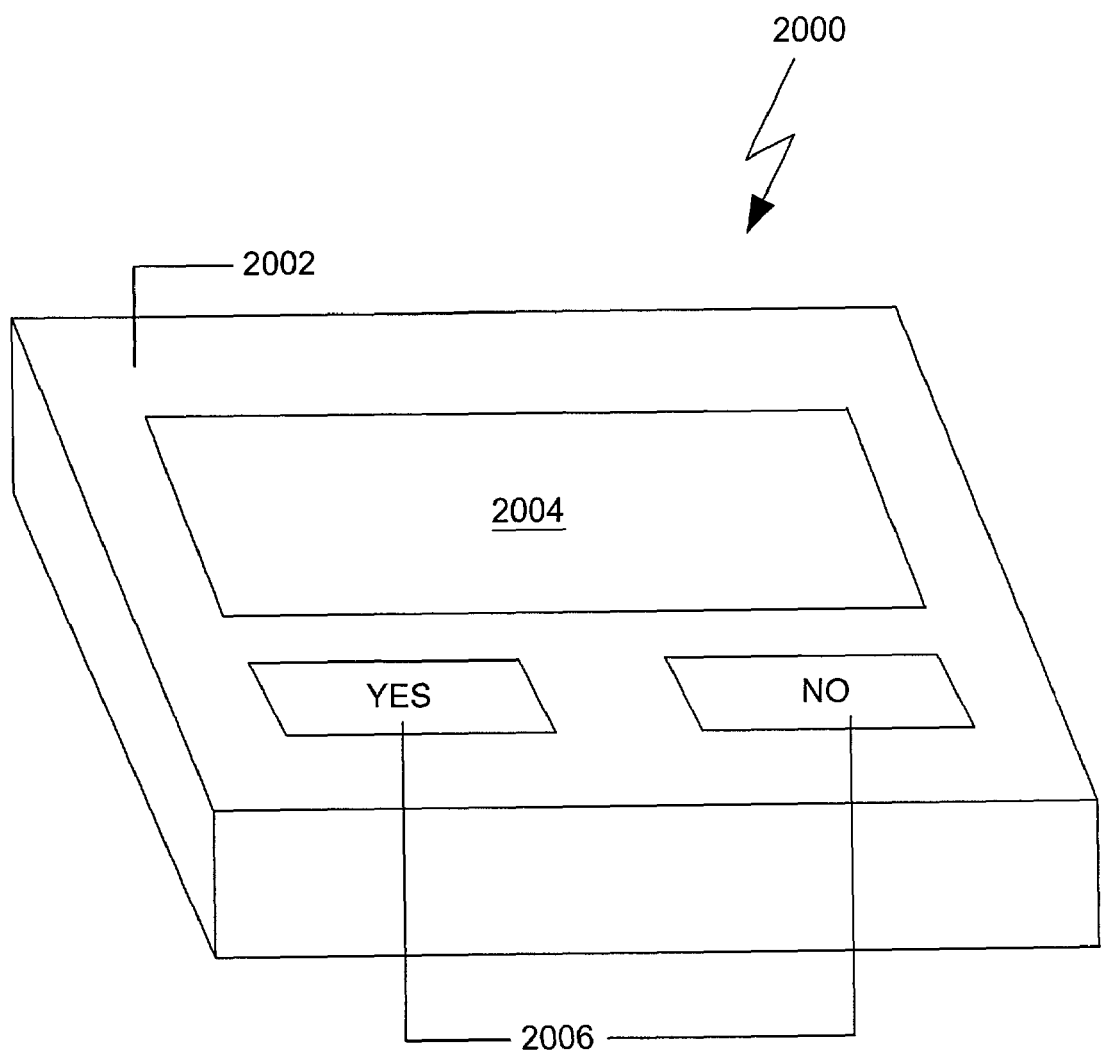
FIG. 20 depicts an embodiment of the present invention, in which a physiological parameter-measuring device is an optional component.

FIG. 20 depicts an embodiment of the patient monitoring apparatus 2000, in which the housing 2002, the output device 2004, and the input device 2006 stand alone as a complete unit. (A physiological parameter-measuring unit, such as a scale, is not required to interface with the unit 2000, but may be added). As in other embodiments, circuitry for operation of the device is held within the housing 2000. The output device 2002 may be a display, such as an LCD screen, and may include an audio output unit. The input device 2006 is depicted as two buttons, a "YES" button and a "NO" button. One skilled in the art understands that the input device may be a keypad, a mouse, a button, a switch, a light pen, or any other suitable input device. In one embodiment of the invention, the input and output devices 2004 and 2006 are combined into a touch-screen device.

The patient monitoring apparatus 2000 of FIG. 20 may be programmed to contain a plurality of question hierarchies, each of which relates to a health-related symptom. Each hierarchy contains a set of questions. Each question in a given hierarchy is aimed at characterizing a particular symptom in a particular way. Certain questions within a hierarchy may be deemed moot (and thus will not be asked) in light of a patient's answer to a previous question. Details regarding question hierarchies will be discussed in greater detail, below.

By programming the patient monitoring apparatus 2000 to contain a plurality of question hierarchies, the unit 2000 attains great flexibility as a tool for monitoring chronic diseases of many varieties. A particular chronic disease may be monitored by asking questions about symptoms associated with the disease. Thus, for example, the unit 2000 may be made to monitor the health status of a patient with chronic obstructive pulmonary desease (COPD) by querying the patient, using questions extracted from question hierarchies relating to symptoms associated with COPD. The same unit 2000 may be used to monitor a patient with diabetes by asking questions extracted from a different set of question hierarchies, which are related to symptoms associated with diabetes.

Figure 21:
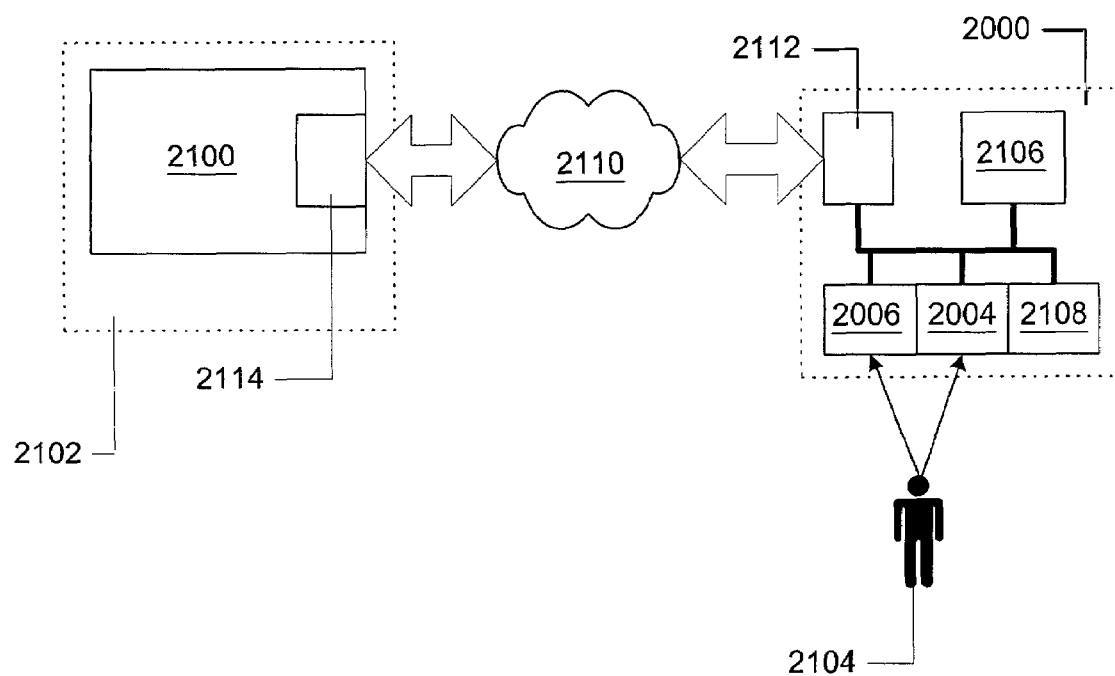
FIG. 21 depicts depicts an embodiment of a system, in which a physiological parameter-measuring device is an optional component.

FIG. 21 is a high-level depiction of a monitoring system employing the embodiment 2000 depicted in FIG. 20, and may be used as a starting point for a more detailed discussion of the patient monitoring apparatus 2000.

As can be seen from FIG. 21, the system comprises a patient monitoring apparatus 2000 and a central computer 2100. The central computer 2100 is housed within a facility 2102 that is located remote from the patient monitoring apparatus 2000. For example, the patient monitoring apparatus 2000 may be located in the home of an ambulatory patient 2104, while the central computer 2100 is located in a health care facility 2102.

As described previously, the patient monitoring apparatus 2000 is composed of a central processor unit 2106, which is in communication with an input device 2006, an output device 2004, and a memory device 2108. The memory device 2108 has a plurality of question hierarchies stored within it, as discussed more fully, below.

As discussed previously, the output device 2004 may be used to prompt the patient 2104 with questions regarding the patient's wellness. The output device 2004 may consist of a visual display unit that displays the questions in a language of the patient's 2104 choosing. Alternatively, the output device 2004 may consist of an audio output unit that vocalizes the questions. In one embodiment, the audio output unit 2004 may vocalize the questions in a language of the patient's 2104 choosing.

The patient monitoring apparatus 2000 communicates with the central computer 2100 via a network 2110; the patient monitoring apparatus 2000 uses a communication device 2112 to modulate/demodulate a carrier signal for transmission via the network 2110, while the central computer uses a communication device 2114 for the same purpose. Examples of suitable communication devices 2112 and 2114 include internal and external modems for transmission over a telephone network, network cards (such as an Ethernet card) for transmission over a local area network, a network card coupled to some form of modem (such as a DSL modem or a cable modem) for transmission over a wide area network (such as the Internet), or an RF transmitter for transmission to a wireless network.

A system composed as described above may be programmed to carry on periodic (e.g., daily) questioning of a patient 2104, with respect to the patient's 2104 perception regarding his or her own status vis-à-vis a particular set of symptoms. For example, a patient suffering from COPD is likely to experience shortness of breath, both during the day and during the night (amongst many other symptoms). Thus, the system may question the patient 2104 about his own percpetions regarding his shortness of breath. The questions used to determine the patient's 2104 judgment about his own shortness of breath during the day are contained in a first question hierarchy. Similarly, questions related to the patient's 2104 shortness of breath during the night are contained in a second question hierarchy.

The first hierarchy, which is related to shortness of breath during the day, may be structured as follows:

TABLE 5

Question Hierarchy: Shortness of Breath During the Day

| Question #1 | Are you feeling more short of breath? |
|---|---|
| Question #2 | Do you feel more short of breath in response to physical exertion? |
| Question #3 | Do you feel more short of breath during periods of rest? |
| Question #4 | Does stress make you feel more short of breath? |

Each of the questions in the hierarchy is related to day-time shortness of breath. The first question is broadly focussed, simply asking "Are you feeling more short of breath?" Clearly, if the patient 2104 were to answer "no" to such a question, the remainder of the questions would be unnecessary. Thus, the system may be designed to prevent the remaining questions from being asked (this will be discussed in greater detail, bleow). Question #2 asks a question that is more particularized than question #1: "Do you feel more short of breath in response to physical exertion?" An affirmative answer to this question is more serious, and provides more particularized information, than an affirmative answer to the broader query presented in question #1. Although not essential, each question hierarchy may be constructed in accordance with this paradigm: (1) a negative answer to a preceeding questions negates the need to ask any additional questions in the hierarchy; (2) successive questions relate to increasingly more particularized aspects of a given symptom; and (3) successive questions relate to an increasing severity level of a given symptom.

Figure 22:
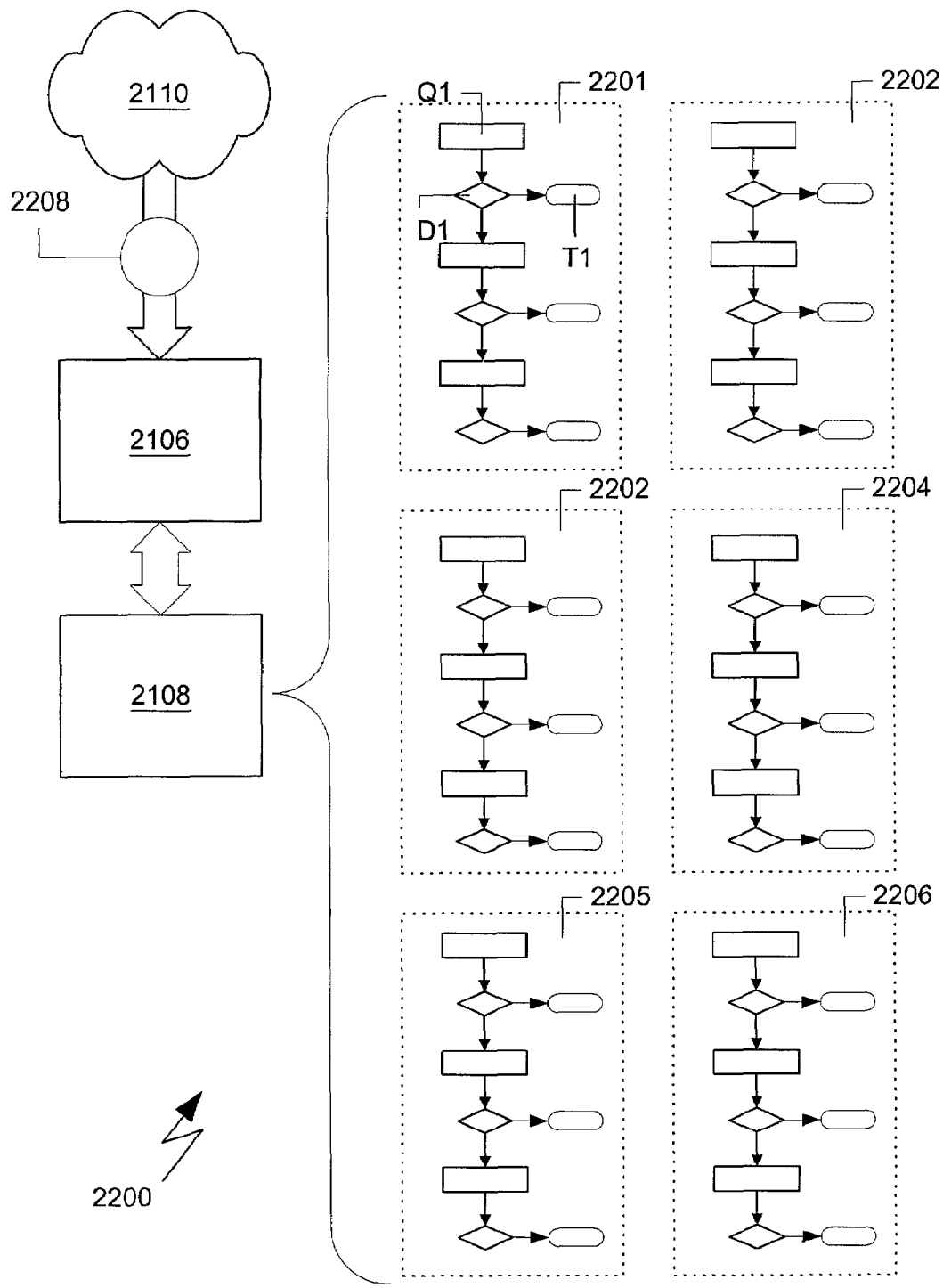
FIG. 22 depicts a memory device programmed with a set of question hierarchies.

FIG. 22 depicts the partial contents of the memory device 2108 of FIG. 21. As can be seen from FIG. 21, the memory device 2108 is programmed with a set of question hierarchies 2200. In the example depicted in FIG. 22, the memory device is programmed with six question hierarchies 2201, 2202, 2203, 2204, 2205, and 2206 (collectively referred to as "the set of question hierarchies 2200"). As described previously, each hierarchy relates to a symptom condition to be monitored, meaning that the number of question hierarchies stored in the memory device 2108 is dependent upon the number of symptoms to be monitored.

Hierarchy 2201 has a basic structure that includes a first question Q1, followed by a first decision point D1. At decision point D1, the patient monitoring apparatus 2000 decides whether or not to ask the subsequent question, Q2. For example, Q1 may be a question that reads "Are you feeling more short of breath?" If the patient 2104 answers "no," this answer is analyzed at decision point D1, and the questioning terminates at terminal point T1. Otherwise, the questioning continues with the next question, Q2, and the process continues.

Each of the hierarchies 2200 depicted in FIG. 22 posssess the above-recited structure, although other structures are possible, some of which are described below. One skilled in the art understands that although each hierarchy 2200 is depicted as consisting of three questions, a hierarchy may consist of any number of questions, including a single question.

As depicted in FIG. 22, the memory device 2108 is in data communication with the monitoring device's 2000 microprocessor 2106, which, in turn, is in data communication with a remote computer 2100 (not depicted in FIG. 22) via a network 2110 and via a communication device 2112 (also not depicted in FIG. 22). The remote computer 2100 transmits a symptom identifier 2208 to the monitoring device's 2000 microprocessor 2106. The symptom identifier 2208 corresponds to a question hierarchy 2200. For example, a symptom identifier with a value of "1" may correspond to hierarchy 2201, while a symptom identifier with a value of "2" corresponds to hierarchy 2202, etc. The microprocessor 2106 responds to having received a symptom identifier 2202 by executing the corresponding hierarchy (i.e., asking a question within the hierarchy, and deciding whether or not to ask a subsequent question therein). Thus, the patient monitoring device 2200 may be made to execute n number of question hierarchies by transmitting to it n number of symptom identifiers.

Given that a known set of symptoms are correlated with any given chronic disease, the patient monitoring device 2000 may be tailored to monitor the health status of a patient 2104 with a particular disease by executing question hiearchies 2200 relating to symptoms corresponding with the patient's 2104 particular disease. Thus, the remote computer 2100 may be programmed with software that presents a menu for each patient 2104. The menu allows the health care provider to select from among a set of chronic diseases. Based upon the selected chronic disease, the remote computer 2100 transmits one or more symptom identifiers (which correspond to symptoms known to accompany the selected disease) to the patient monitoring apparatus 2000. The remote computer 2100 receives the patient's 2104 responses, and scores the response in accordance with a scoring algorithm, discussed in detail below. Based upon the outcome of the score, an exception report may be generated, meaning that a health care provider will be notified of the patient's possible need for assistance. Alternatively, the remote computer 2100 may be programmed to transmit an e-mail message or a numeric page to communicate the information concerning the patient 2104. In principle, any data transmission communicating the patient's 2104 potential need for assistance may be transmitted.

In certain situations, it may be desirable for the patient monitoring device 2000 to obtain information regarding a physiological paramter. For example, if a particular chronic disease is associated with a fever, the patient monitoring device may want to know information concerning the patient's 2104 body temperature. Two general approaches exist for gaining information concerning a physiological paramter. The monitoring system 2000 may be adapted for interfacing with a physiological parameter-measuring unit, as has been disclosed with reference to other embodiments of the invention. The parameter-measuring unit can then directly measure the physiological parameter and transmit the data to the central computer 2100. Many times, this is an appropriate approach. Accordingly, according to one embodiment of the invention, the microprocessor 2106 may interface with a physiological parameter-measuring device, such as a scale or a thermometer, as previously described herein. On the other hand, oftentimes it is possible to ask the patient to measure the parameter for himself (e.g., take his own temperature). This approach has an advantage, in that the cost of obtaining the information is minimized. This approach is particularly useful when an exact measurement of a physiological parameter is not as useful as simply knowing whether the parameter crosses some threshold. Under these circumstances, the cost of directly obtaining precise information may outweigh the financial benefit of knowing such information. Thus, as depicted in FIG. 23, a question hierarchy 2200 may be designed to ask a patient whether one of his physiological parameters exceeds a threshold, T.

Figure 23:
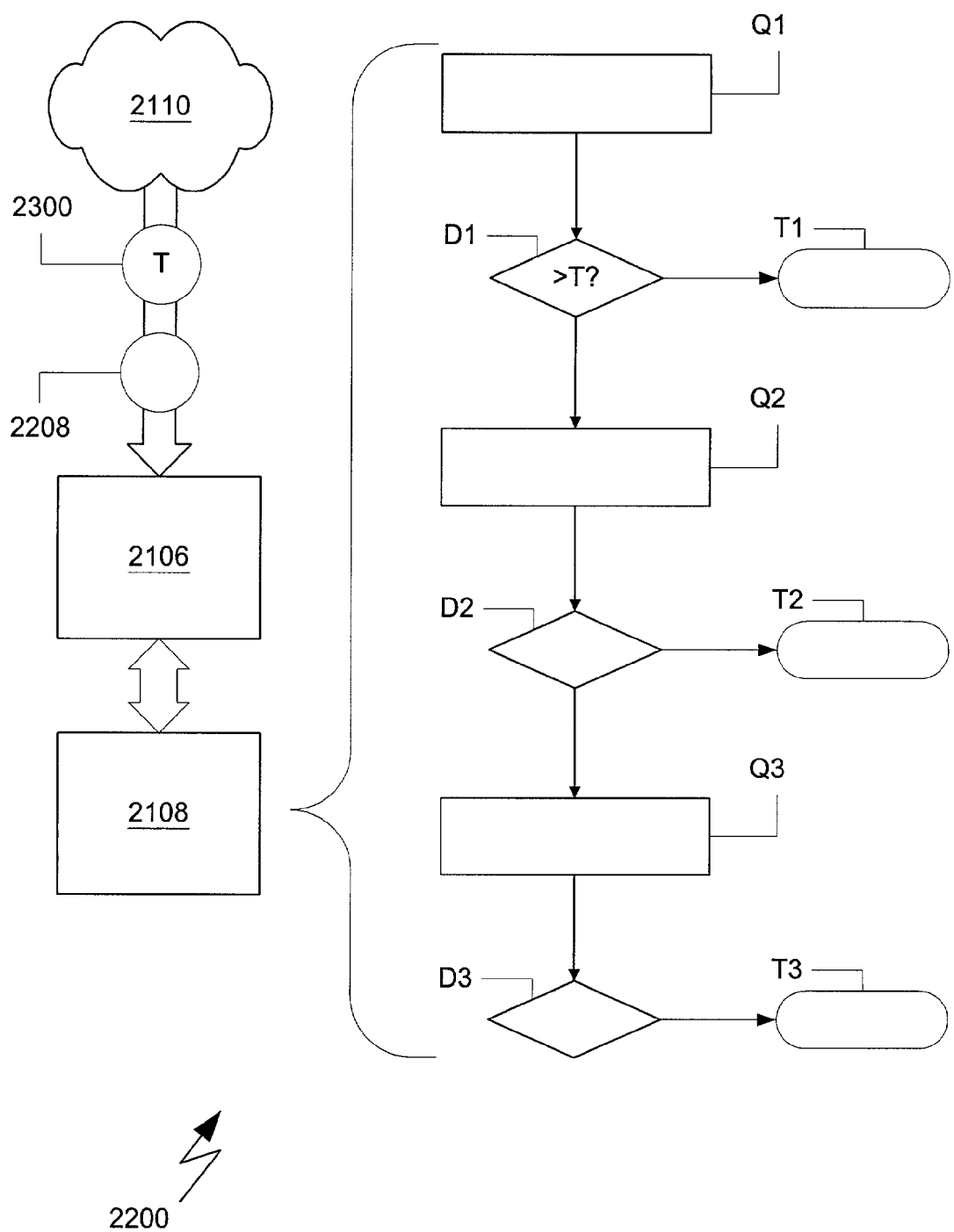
FIG. 23 depicts a particular question hierarchy logical structure, according to one embodiment of the present invention.

The question hierarchy 2200 depicted in FIG. 23 is similar to the question hierarchies 2200 discussed with reference to FIG. 22. The question hierarchy 2200 corresponds to a symptom identifier 2208, which is transmitted to the patient monitoring device 2000 by a remote computer 2100. The hierarchy 2200 possesses several questions Q1, Q2, and Q3, some of which may go unasked, if a decision point D1, D2, or D3 terminates the flow of questioning by transferring execution flow to a terminal point T1, T2 or T3. Of particular note in the question hierarchy 2200 of FIG. 23 is the first question, Q1, and the first decision point D1. The first question, Q1, asks the patient 2104 if a particular physiological parameter of his exceeds a given threshold, T. The value represented by T is transmitted to the patient monitoring device 2000 by the remote computer 2100, as is depicted by threshold datum 2300. Therefore, to invoke this particular hierarchy 2200, the remote computer should transmit both a symptom identifier 2208 and a threshold datum 2300. In response, the patient monitoring device 2000 responds by asking the patient 2104 if his particular physiological paramter exceeds the threshold, T. Next, as is depicted by decision point D1, the patient monitoring device 2000 determines whether or not to proceed with further questions, on the basis of whether or not the parameter exceeded the threshold, T.

Another situation likely to arise in the context of monitoring a patient 2104 with a chronic illness is that the patient 2104 is to be queried regarding his faithfulness to a prescribed health care regimen. For example, if the patient 2104 is a diabetic, the patient is likely to be on a strict diet. The patient monitoring device 2000 may be programmed to ask the patient 2104 if he has been following his diet. If the patient 2104 answers "yes," the device 2000 may respond by praising the patient 2104—a tactic that may be particularly advantageous for young patients. On the other hand, if the patient 2104 answers "no," the device 2000 may respond by reminding the patient 2104 to adhere to his diet.

Figure 24:
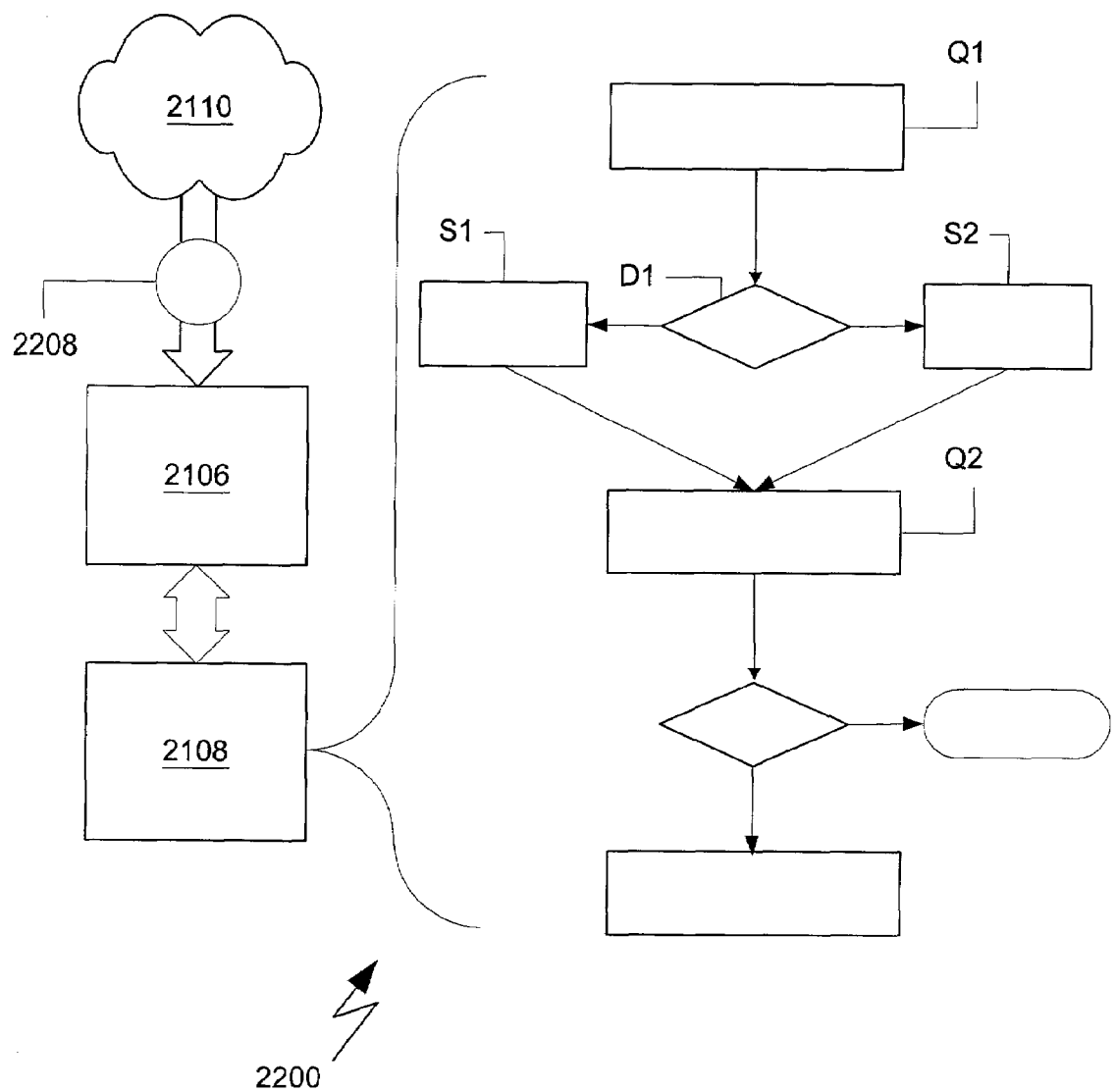
FIG. 24 depicts another question hierarchy logical structure, according to one embodiment of the present invention.

FIG. 24 depicts a question hierarchy 2200 designed to achieve the results of praising a patient 2104 for adhering to a prescribed regimen, or reminding the patient 2104 of the importance of adhering thereto. Of particular note in the question hierarchy 2200 depicted in FIG. 24 is the first question, Q1. The first question, Q1, asks the patient 2104 if he has been adhering to a health care regimen (such as, a diet or a medication regimen). Next, at decision point D1, flow of execution is adjusted based upon whether or not the patient 2104 has been adhering to the regimen. If the patient 2104 has been adhering to the regimen, the patient 2104 is presented with a statement, S1, praising the patient. Otherwise, the patient 2104 is presented with a statement, S2, reminding the patient 2104 to adhere to his regimen. In either event, execution flow is passed to the second question, Q2, and hierarchy execution continues in accordance with the flow described with reference to FIG. 22.

Figure 25:
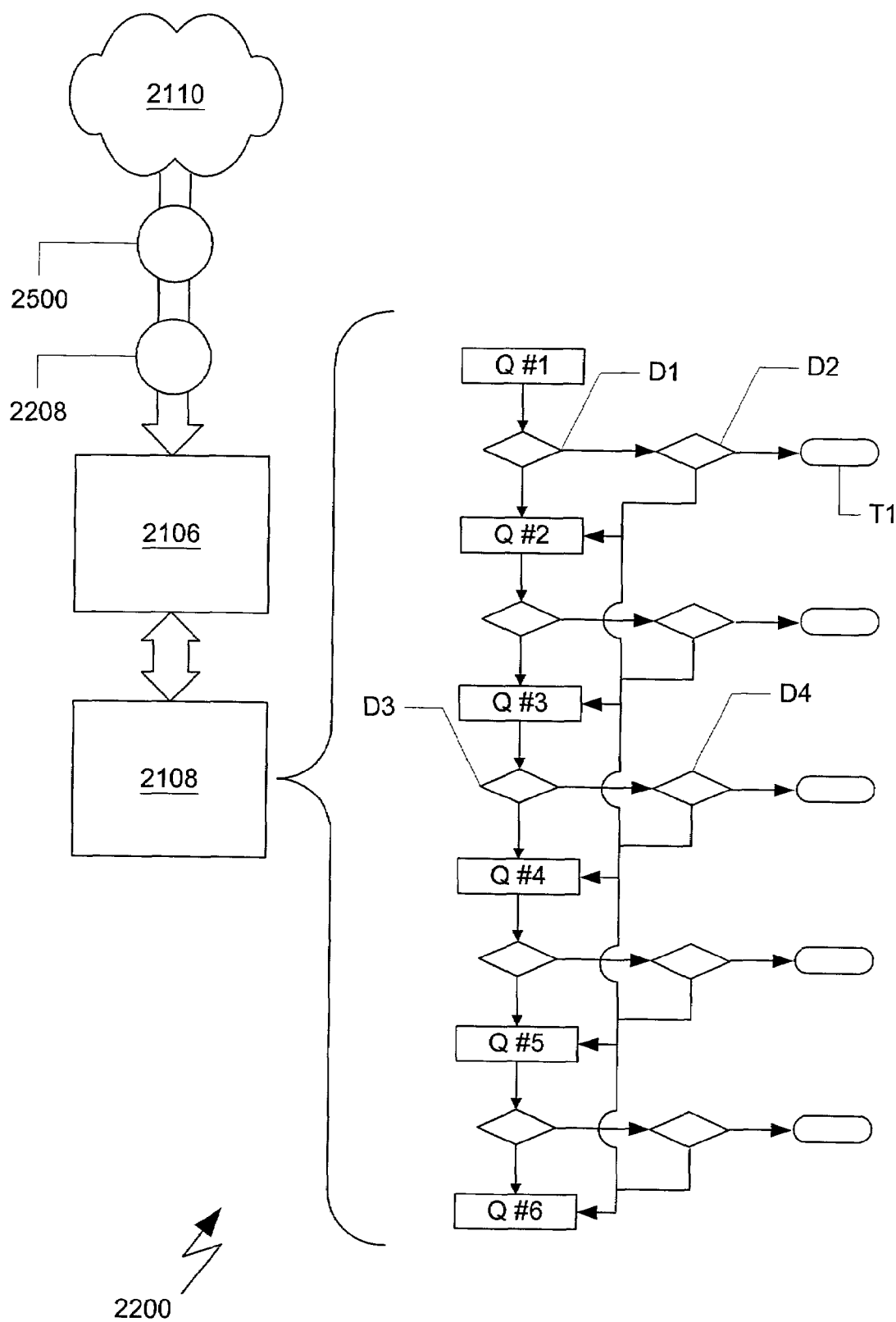
FIG. 25 depicts another question hierarchy logical structure, according to one embodiment of the present invention.

FIG. 25 depicts a question hierarchy 2200 that has been modified to permit the remote computer 2100 to command specific questions within the hierarchy 2200 to be asked, regardless of any answer that may have been previously given by the patient 2104. To achieve this result, the remote computer 2100 should transmit a symptom identifier 2208 corresponding to the question hierarchy 2200. Additionally, a question set 2500 should be transmitted. The question set 2500 may define a set of questions to be forced "on." For example, the question set 2500 may be {3, 5}, meaning that questions 3 and 5 are to be asked, no matter what the patient 2104 has previously answered.

Continuing the discussion assuming that a question set 2500 of {3, 5} had been transmitted, execution of the hierarchy commences with the asking of the first question, Q1. Next, at decision point D1, the patient's 2104 answer to the first question is assessed to determine whether the subsequent question in the hierarchy should be asked. If the answer is such that ordinarily none of the remaining questions should be asked, execution would typically flow to terminal point T1. However, in this embodiment, a second decision point, D2, is interposed between decision point D1 and terminal point T1. At the second decision point, D2, it is determined whether the question set 2500 contains a question number that is higher than the question number that was just asked. In the case of the present example, the question set 2500 contains two such question numbers, because question numbers 3 and 5 are higher than the present question number, 1. If the question set 2500 does contain a question number that is higher than the question number just asked, then execution flows to the smallest such question number (in this case, question number 3, Q3). Thereafter the process repeats, thereby ensuring that each of the question numbers in the question set will be asked.

Figure 26:
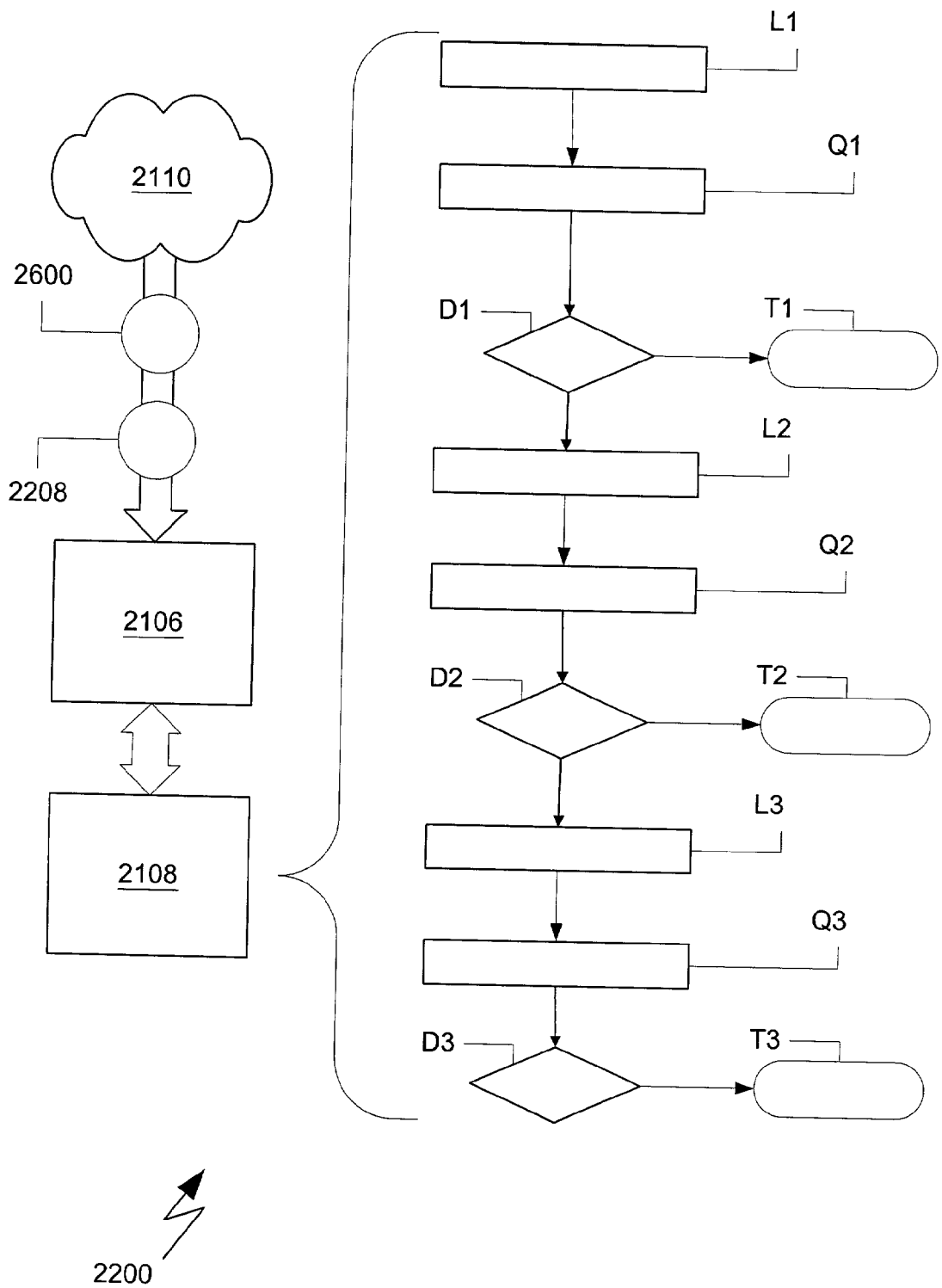
FIG. 26 depicts yet another question hierarchy logical structure, according to one embodiment of the present invention.

FIG. 26 depicts a question hierarchy 2200 that has been modified to permit the remote computer 2100 to command a specific sequence in which the questions within the hierarchy 2200 should be asked. To achieve this result, the remote computer 2100 should transmit a symptom identifier 2208 corresponding to the question hierarchy 2200. Additionally, a sequence set 2600 should be transmitted. The sequence set 2600 is a set of data defining the order in which the questions are to be asked. For example, the sequence set 2600 may be {3, 1, 2}, meaning that the question that would ordinarily be asked third should be asked first, that the question that would ordinarily be asked first should be asked second, and that the question that would ordinarily be asked second should be asked third.

Continuing on with the example, execution of the hierarchy 2200 of FIG. 26 commences with a look-up operation, L1. During the look-up operation L1, the first element of the sequence set 2600 is used to index into an array containing the questions within the hierarchy. In the present example, since "3" is the first element of the sequence set, the third question from the array is retrieved. Next, the retrieved question (identified as Q1 in FIG. 26) is asked, and execution of the hierarchy proceeds as has been generally described with reference to FIG. 22. Thus, by inserting a look-up operation L1, L2, or L3 prior to each questioning operation Q1, Q2, or Q3, any desired sequence of questioning may be commanded.

The question hierarchies disclosed in FIGS. 22-26 may be programmed into the memory device 2108 of the patient monitoring device 2000, thereby obviating the need to transmit the text of the questions from the central computer 2100 to the patient monitoring device 2000. One skilled in the art understands that the question hiearchies 2200 may be implemented in the form of an application-specific integrated circuit, as well. Optionally, the questions within the hierarchies 2200 may written to be answered with either a "yes" or "no," achieving the advantage of simplifying the input required from the patient 2104, and thereby necessitating only "yes" or "no" buttons for the input device 2006. Further, any of the preceeding question hierarchies 2200 forms may be combined.

As described earlier, the memory device 2108 may store each of the question hierarchies 2200 in a plurality of languages, so as to permit patients 2104 of many nationalities to use the device 2000. If the output device 2004 is an audio output unit, the questions within each of the question hierarchies 2200 may be stored in a digital audio format in the memory device 2108. Accordingly, the questions are presented to the patient 2104 as a spoken interogatory, in the language of the patient's 2104 choice.

Figure 27:
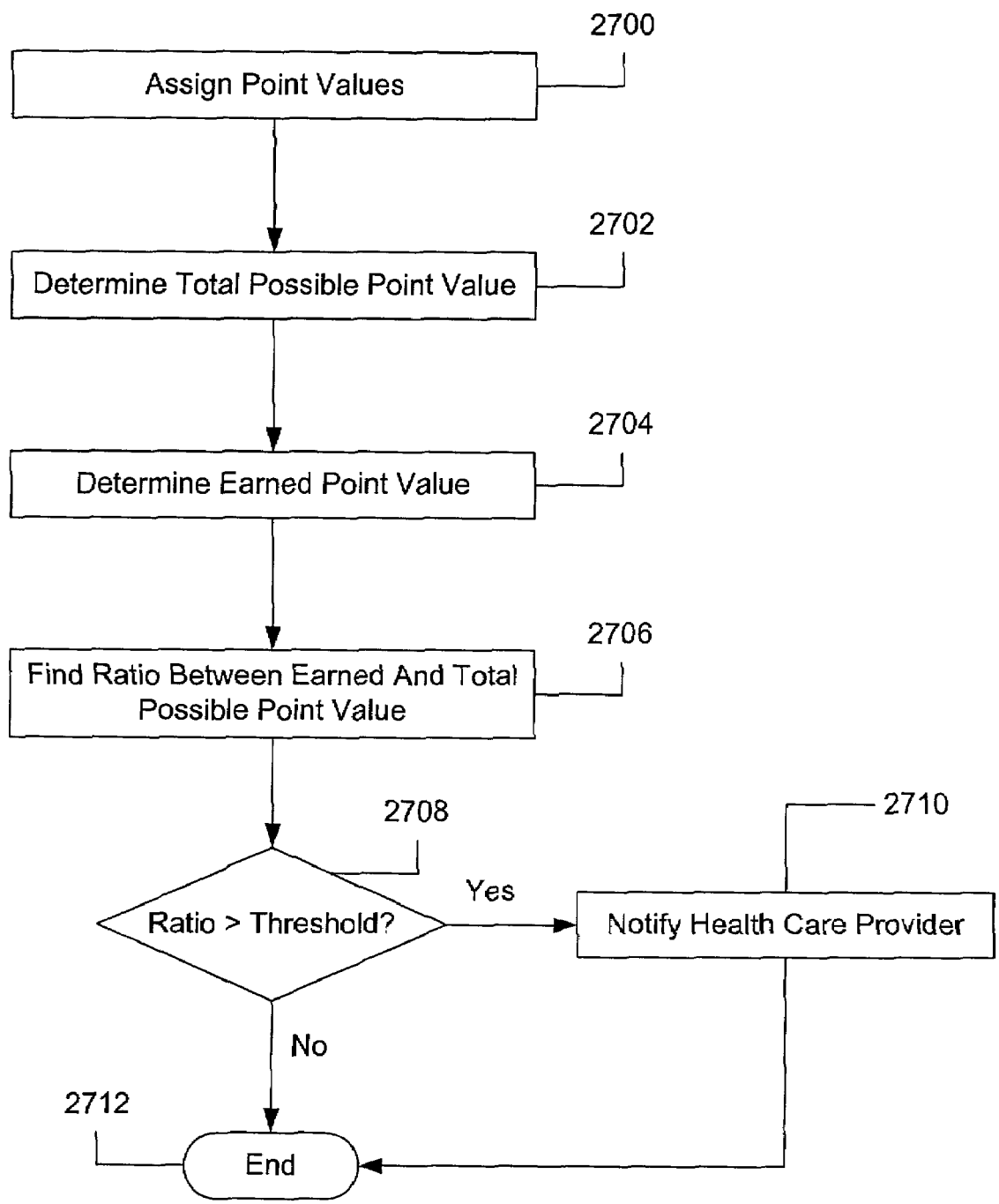
FIG. 27 depicts one method of determing whether a patient is in need of medical assistance, based upon the patient's response to questions presented from a question hierarchy.

FIG. 27 depicts a method by which the patient's 2104 answers to the questions presented in the hierarchies 2200 may be analyzed. As mentioned earlier, depending upon the outcome of the analysis, an exception report may be issued and a health care provider may be notified. According to the method depicted in FIG. 27, during operation 2700 a point value is assigned to each question in each of the invoked question hierarchies 2200. The points assigned to a given question are "earned" by a patient 2104, if the patient answers the question in a particular way. Otherwise, no points are earned. For example, an affirmative response to the question "are you experiencing shortness of breath?" may be worth 10 points, while a negative response to that question is worth nothing. A standard point value may be assigned to each question (each question has a point value of 10, for instance), or different questions may be assigned different point values (a first question is worth 10 points, while a question directed toward a more serious issue may be worth 30 points, for example). A default point assignment scheme may be presented for approval by a health care provider. The health care provider may then adjust the point assignment scheme to fit the needs of an individual patient 2104.

In operation 2702, the point value of each of the questions actually asked to the patient 2104 is determined. Thus, questions that were not asked to a patient 2104 are not included in this point total. In operation 2704, the patient's 2104 earned point value is totaled. Then, in operation 2706, the patient's 2104 earned point total (determined in operation 2704) is divided by the total possible point value (determined in operation 2702).

In operation 2708, it is determined whether the fraction found in operation 2706 exceeds a threshold (as with the point assignment scheme, the threshold may be defined by the health care provider). If so, the patient's health care provider is notified (perhaps by the issuance of an exception report), as shown in operation 2710. Finally, the process terminates in operation 2712.

Figure 28:
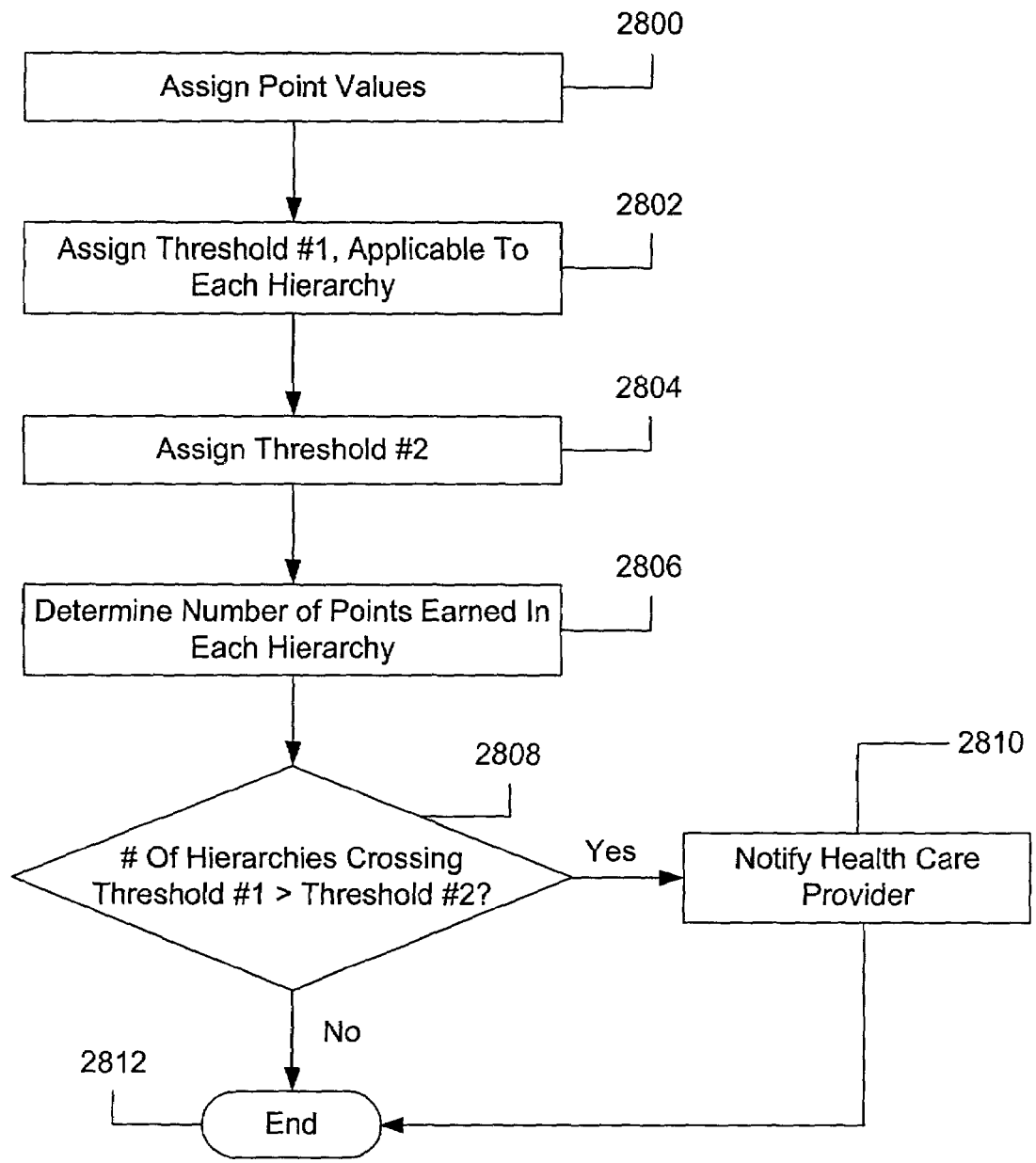
FIG. 28 depicts another method of determing whether a patient is in need of medical assistance, based upon the patient's response to questions presented from a question hierarchy.

FIG. 28 depicts another method by which the patient's 2104 answers to the questions presented in the hierarchies 2200 may be analyzed. According to the method depicted in FIG. 28, during operation 2800 a point value is assigned to each question in each of the invoked question hierarchies 2200. The details of the point assignment scheme are identical to those in operation 2700 of FIG. 27.

Next, in operation 2802, a threshold is assigned to each invoked hierarchy 2200. Again, this threshold may be assigned by default, and the health care provider may be given an option to adjust this threshold. The threshold of operation 2802 applies to each hierarchy 2200, meaning that a decision will be made, on a hierarchy-by-hierarchy basis, whether the patient 2104 has accummulated sufficient points in a particular hierarchy to cross a threshold assigned to that hierarchy 2200. In operation 2804, a second threshold is assigned. The threshold of operation 2804 relates to the number of hierarchies 2200 that may be allowed to exceed the threshold of operation 2802.

In operation 2806, the number of points earned by the patient 2104 in each hierarchy 2200 is determined. Then in operation 2808, it is determined whether the number of hierarchies 2200 in which the threshold of operation 2802 was crossed exceeds the threshold of operation 2804. If so, the patient's health care provider is notified, as shown in operation 2810. Finally, the process terminates in operation 2812.

The methods of FIGS. 27 and 28 are preferably performed by the remote computer 2100, although they may be performed by any other processing device. The aforementioned methods are preferably embodied as software stored in a memory device within the central computer 2100. However, they may be embodied on a computer-readable medium, such as a compact disc, a floppy disc, a network cable, or any other form of media readable by a computer.

Thus, it will be appreciated that the previously described versions of the invention provide many advantages, including addressing the needs in the medical profession for an apparatus and method capable of monitoring and transmitting physiological and/or wellness parameters of ambulatory patients to a remote site whereby a medical professional caregiver can evaluate such physiological and wellness parameters and make decisions regarding the patient's treatment.

Also, it will be appreciated that the previously described versions of invention provide other advantages, including addressing the need for an apparatus for monitoring and transmitting such physiological and/or wellness parameters that is available in an easy to use portable integrated single unit.

Also, it will be appreciated that the previously described versions of the invention provide still other advantages, including addressing the need for medical professional caregivers to monitor and manage the patient's condition to prevent the rehospitalization of the patient, and to prevent the patient's condition from deteriorating to the point where hospitalization may be required.

Although the invention has been described in considerable detail with reference to certain preferred versions thereof, other versions are possible. For example a weight management and control apparatus.

Therefore, the spirit and scope of the appended claims should not be limited to the description of the preferred versions contained herein.

The claimed invention is:

1. A patient monitoring apparatus for monitoring a health condition of an ambulatory patient, the patient monitoring apparatus comprising:
   a display for presenting questions to the ambulatory patient;

an input device permitting the ambulatory patient to enter answers to the questions;

a microprocessor operably coupled to the display and the input device;

a read-only memory device operably coupled to the microprocessor, the read-only memory device storing a plurality of question hierarchies, each of the question hierarchies corresponding to a symptom in a plurality of symptoms, wherein a first question hierarchy in the plurality of question hierarchies corresponds to a first symptom in the plurality of symptoms, wherein the first question hierarchy includes a first question that solicits information regarding the first symptom, and wherein the first question hierarchy includes a second question that solicits additional information regarding the first symptom; and a communication device operably coupled to the microprocessor;

wherein the microprocessor is programmed to:
receive a symptom identifier from a central computing system via the communication device, the symptom identifier identifying a symptom in the plurality of symptoms;
determine whether the symptom identifier identifies the first symptom;
ask the first question when the symptom identifier identifies the first symptom;
receive an answer to the first question via the input device, the first question hierarchy indicating that the second question is moot when the answer to the first question indicates a first option, the first question hierarchy indicating that the second question is not moot when the answer to the first question indicates a second option;
make a decision regarding whether the second question is moot in light of the answer to the first question;
automatically ask the second question when the patient monitoring apparatus makes the decision that the second question is not moot in light of the answer to the first question, the patient monitoring apparatus not asking the second question when the patient monitoring apparatus makes the decision that the second question is moot in light of the answer to the first question; and
send to the central computing system a set of answers, the set of answers comprising answers to each question in the first question hierarchy asked by the patient monitoring apparatus, the central computing system configured to determine, based on the set of answers, whether to notify a health care provider that the ambulatory patient possibly needs medical care.

2. The patient monitoring apparatus device of claim 1, wherein each question within the first question hierarchy is answerable via a response selected from a set consisting of "yes" and "no."

3. The patient monitoring apparatus of claim 1, wherein an answer to the second question indicates whether the first symptom is more severe than indicated by the answer to the first question.

4. The patient monitoring apparatus of claim 1, wherein one of the questions within the first question hierarchy asks whether a physiological parameter of the ambulatory patient exceeds a threshold.

5. The patient monitoring apparatus of claim 4, wherein the patient monitoring apparatus receives the threshold from the central computing system via the communication device.

6. The patient monitoring apparatus of claim 1, wherein one of the questions within the first question hierarchy asks whether the ambulatory patient is adhering to a pre-established health care regimen.

7. The patient monitoring apparatus of claim 6, wherein the microprocessor is programmed to praise the ambulatory patient, in response to the ambulatory patient indicating that the ambulatory patient is adhering to the pre-established health care regimen.

8. The patient monitoring apparatus of claim 1, wherein the second question asks about the first symptom with more specificity than the first question.

9. The patient monitoring apparatus of claim 1, wherein the microprocessor is programmed to ask one or more questions within the first question hierarchy, regardless of any answer to any other question within the first question hierarchy.

10. The patient monitoring apparatus of claim 1, wherein the microprocessor is programmed to:
receive a sequence set from the central computing system, the sequence set being a set of data defining an order in which the patient monitoring apparatus is to ask questions in the first question hierarchy; and
ask questions within the first question hierarchy in the order.

11. The patient monitoring apparatus of claim 1,
wherein the first question hierarchy includes a reminder to the ambulatory patient to perform a particular act, the reminder requiring no answer from the ambulatory patient: and wherein the microprocessor is programmed to present the reminder when the microprocessor receives from the ambulatory patient a particular answer to a question in the first question hierarchy.

12. The patient monitoring apparatus of claim 1, wherein the read-only memory device stores each of the question hierarchies in a plurality of languages.

13. The health care device patient monitoring apparatus of claim 1, wherein:
the read-only memory device stores the first question in a digital audio format;
the patient monitoring device further comprises an audio output unit operably coupled to the microprocessor; and
the microprocessor is further programmed to ask the first question at least in part by causing the audio output unit to play back the first question, so that the patient monitoring apparatus vocalizes the first question to the ambulatory patient.

14. The patient monitoring apparatus of claim 1, wherein the input device comprises:
a first button to indicate an answer in the affirmative; and
a second button to indicate an answer in the negative.

15. The patient monitoring apparatus of claim 1, further comprising:
a physiological parameter measuring device operably coupled to the microprocessor;
wherein the physiological parameter measuring device produces a measured parameter by measuring a physiological parameter of the ambulatory patient, the physiological parameter measuring device transferring the measured parameter to the microprocessor, the microprocessor transmitting the measured parameter to the central computing system, the central computing system using the measured parameter to determine whether to notify the health care provider that the ambulatory patient possibly needs medical care.

16. The patient monitoring apparatus of claim 15, wherein the physiological parameter measuring device is a scale.

17. A health care system for monitoring a health condition of an ambulatory patient, the health care system comprising:
a patient monitoring apparatus; and
a central computing system in communication with the patient monitoring apparatus, the patient monitoring apparatus comprising:
a first display for presenting questions to the ambulatory patient;
a first input device permitting the ambulatory patient to enter answers to the questions;
a first microprocessor operably coupled to the first display and the first input device;
a read-only memory device operably coupled to the first microprocessor, the read- only memory device storing a plurality of question hierarchies, each of the question hierarchies corresponding to a symptom in a plurality of symptoms,
wherein a first question hierarchy in the plurality of question hierarchies corresponds to a first symptom in the plurality of symptoms,
wherein the first question hierarchy includes a first question, the first question soliciting information regarding the first symptom,
wherein the first question hierarchy includes a second question, the second question soliciting additional information regarding the first symptom; and
a communication device operably coupled to the first microprocessor; wherein the first microprocessor is programmed to:
receive a symptom identifier from the central computing system via the communication device, the symptom identifier identifying a symptom in the plurality of symptoms;
determine whether the symptom identifier identifies the first symptom;
ask the first question on the first display when the symptom identifier identifies the first symptom;
receive an answer to the first question via the first input device, the first question hierarchy indicating that the second question is moot when the answer to the first question indicates a first option, the first question hierarchy indicating that the second question is not moot when the answer to the first question indicates a second option;
make a decision regarding whether the second question is moot in light of the answer to the first question; and
automatically ask the second question on the first display when the patient monitoring apparatus makes the decision that the second question is not moot in light of the answer to the first question, the patient monitoring apparatus not asking the second question when the patient monitoring apparatus makes the decision that the second question is moot in light of the answer to the first question; and
the central computer system programmed to:
transmit the symptom identifier to the patient monitoring apparatus, thereby causing the patient monitoring apparatus to ask one or more questions within the one of the question hierarchies corresponding to the symptom identified by the symptom identifier;
receive a set of answers from the patient monitoring apparatus, the set of answers comprising answers to each question in the first question hierarchy asked by the patient monitoring apparatus; and
determine, based on the set of answers, whether to notify a health care provider that the ambulatory patient possibly needs medical care.

18. The health care system of claim 17,
wherein the central computer system comprises:
a second display; and
a second input device; and wherein the central computer system is programmed to:
present a menu of health conditions on the second display;
receive a selection from a user via the second input device, the selection indicating a health condition in the menu of health conditions; and
based upon the health condition, transmit one or more symptom identifiers to the patient monitoring apparatus, thereby causing the patient monitoring apparatus to ask one or more questions within one or more of the question hierarchies corresponding to the one or more symptoms identified by the one or more symptom identifiers.

19. The health care system of claim 17, wherein the central computer system is programmed to determine whether to notify the health care provider that the ambulatory patient possibly needs medical care by being programmed to:
assign a point value to each question within each of the question hierarchies, wherein the point value is earned if the question to which the point value is assigned is answered in accordance with a pre-defined answer;
determine a total point value, the total point value being a sum of the point values assigned to each question in the question hierarchies asked to the ambulatory patient by the patient monitoring apparatus;
determine a total earned point value, the total earned point value being a sum of all earned point values assigned to each question in the question hierarchies asked to the ambulatory patient by the patient monitoring apparatus;
determine a ratio between the total earned point value and the total point value; and notify the health care provider if the ratio exceeds a threshold.

20. The health care system of claim 17, wherein the central computer system is programmed to determine whether to notify the health care provider that the ambulatory patient possibly needs medical care by being programmed to:
assign a point value to each question within each of the question hierarchies, wherein the point value is earned if the ambulatory patient answers the question to which the point value is assigned in accordance with a pre-defined answer;
assign threshold values to each of the question hierarchies;
determine a number of point values earned in each of the question hierarchies, based upon answers given by the ambulatory patient to questions in the question hierarchies asked to the ambulatory patient by the patient monitoring apparatus; and
notify the health care provider if the number of point values earned within more than a pre-defined number of the question hierarchies crosses the threshold values assigned to the question hierarchies.

21. A method for monitoring a health condition of an ambulatory patient, the method comprising:
storing, at a read-only memory device at a patient monitoring apparatus, a plurality of question hierarchies, wherein each of the question hierarchies corresponds to a symptom in a plurality of symptoms,
wherein a first question hierarchy in the plurality of question hierarchies corresponds to a first symptom in the plurality of symptoms, wherein the first question hierarchy includes a first question, the first question soliciting information regarding the first symptom, and wherein the first question hierarchy includes a second question, the second question soliciting additional information regarding the first symptom;

receiving, at the patient monitoring apparatus, a symptom identifier from a central computer system, the symptom identifier identifying a symptom in the plurality of symptoms;

retrieving, by the patient monitoring apparatus, from the read-only memory device, the first question when the symptom identifier identifies the first symptom;

asking, by the patient monitoring apparatus, the first question to the ambulatory patient;

receiving, at the patient monitoring apparatus, an answer to the first question from the ambulatory patient, the first question hierarchy indicating that the second question is moot when the answer to the first question indicates a first option, the first question hierarchy indicating that the second question is not moot when the answer to the first question indicates a second option;

making, at the patient monitoring apparatus, a decision regarding whether the second question is moot in light of the answer to the first question;

automatically asking, by the patient monitoring apparatus, the second question to the ambulatory patient when the patient monitoring apparatus makes the decision is made that the second question is not moot in light of the answer to the first question, the patient monitoring apparatus not asking the second question when the patient monitoring apparatus makes the decision that the second question is moot in light of the answer to the first question; and sending, by the patient monitoring apparatus to the central computing system, a set of answers to each question in the first question hierarchy asked by the patient monitoring apparatus, the central computing system configured to determine, based on the set of answers, whether the ambulatory patient possibly needs medical assistance, and to notify a health care provider when the ambulatory patient possibly needs medical assistance.

22. The method of claim 21, wherein each question within the first question hierarchy is answerable via a response selected from a set consisting of "yes" and "no."

23. The method of claim 21, wherein an answer to the second question determines whether the first symptom is more severe than indicated by the answer to the first question.

24. The method of claim 21, wherein one of the questions within the first question hierarchy asks whether a physiological parameter of the ambulatory patient exceeds a threshold.

25. The method of claim 24, further comprising receiving, at the patient monitoring apparatus, the threshold from the central computer system, the central computer system located at a health care facility.

26. The method of claim 21, further comprising asking, by the patient monitoring apparatus, whether the ambulatory patient is adhering to a pre-established health care regimen.

27. The method of claim 26, further comprising praising, by the patient monitoring apparatus, the ambulatory patient, in response to the ambulatory patient indicating that the ambulatory patient is adhering to the pre-established health care regiment.

28. The method of claim 21, wherein the second question asks about the first symptom with more specificity than the first question.

29. The method of claim 21, further comprising asking, by the patient monitoring apparatus, at least one question within the first question hierarchy, regardless of any answer to any other question within the first question hierarchy.

30. The method of claim 21, further comprising asking, by the patient monitoring apparatus, questions in the first question hierarchy according to a sequence commanded by the central computing system.

31. The method of claim 21, further comprising presenting, by the patient monitoring apparatus, a reminder to the ambulatory patient to perform a particular act when the patient monitoring apparatus receives from the ambulatory patient a particular answers to a given question in the first question hierarchy.

32. The method of claim 21, wherein asking the first question to the ambulatory patient comprises playing back, by the patient monitoring apparatus, an audio clip that vocalizes the first question to the ambulatory patient.

33. The method of claim 21, wherein the method further comprises:

measuring, by the patient monitoring apparatus, a physiological parameter of the ambulatory patient: and transmitting, by the patient monitoring apparatus, the physiological parameter to the central computing system, the central computing system configured to determine whether the ambulatory patient possibly needs medical assistance based on the set of answers and on the physiological parameter.

34. The method of claim 33, wherein measuring the physiological parameter comprises weighing, by the patient monitoring apparatus, the ambulatory patient.

35. A method for monitoring a health condition of an ambulatory patient, the method comprising:

displaying, by a central computing system, a menu of health conditions;

prompting, by the central computing system, a user to select a health condition from the menu of health conditions; and transmitting, by the central computing system, a symptom identifier to a patient monitoring apparatus containing a read-only memory, the symptom identifier identifying a first symptom in a plurality of symptoms, the first symptom associated with the health condition, the read-only memory storing a plurality of question hierarchies, each question hierarchy corresponding to each of a plurality of symptoms, a first question hierarchy in the plurality of question hierarchies corresponding to the first symptom, the first question hierarchy including a first question and a second question, the first question soliciting information regarding the first symptoms, the second question soliciting additional information regarding the first symptom, the patient monitoring apparatus configured to:

determine, in response to receiving the symptom identifier from the central computing system, whether the symptom identifier identifies the first symptom;

ask the first question to the ambulatory patient when the symptom identifier identifies the first symptom;

receive an answer to the first question, the first question hierarchy indicating that the second question is moot when the answer to the first question indicates a first option, the first question hierarchy indicating that the second question is not moot when the answer to the first question indicates a second option;

make a decision regarding whether the second question is moot in light of the answer to the first question, automatically ask the second question when the decision is made that the first question hierarchy indicates that the second question is not moot in light of the answer to the first question, the patient monitoring apparatus not asking the second question when the patient monitoring apparatus makes the decision that the second question is moot in light of the answer to the first question; and send to the central computing system a set of answers to each question in the first question hierarchy asked by the patient monitoring apparatus; receiving, at the central computing system, the set of answers;

determining, at the central computing system, based on the set of answers whether the ambulatory patient is possibly in need of medical assistance; and notifying, by the central computing system, a health care provider when the ambulatory patient is possibly in need of medical assistance.

36. A method of analyzing a set of answers to questions drawn from a plurality of question hierarchies, each of the question hierarchies corresponding to a symptom in a plurality of symptoms, the method comprising:

asking, at the patient monitoring apparatus, a first question in a first question hierarchy in the plurality of question hierarchies, the first question hierarchy corresponding to a first symptom in the plurality of symptoms;

receiving, at the patient monitoring apparatus, an answer to the first question, the first question soliciting information regarding the first symptom, the first question hierarchy including a second question, the second question soliciting additional information regarding the first symptom, each question in the first question hierarchy being assigned a point value, the first question hierarchy indicating that the second question is moot when the answer to the first question indicates a first option, the first question hierarchy indicating that the second question is not moot when the answer to the first question indicates a second option, making, by the patient monitoring apparatus, a decision based on the answer to the first question, the decision regarding whether the second question is moot in light of the answer to the first question;

automatically asking, by the patient monitoring apparatus, the second question when the monitoring apparatus makes the decision that the second question is not moot in light of the answer to the first question, the patient monitoring apparatus not asking the second question when the patient monitoring apparatus makes the decision that the second question is moot in light of the answer to the first question;

sending, by the patient monitoring apparatus, the set of answers to a central computing system, the set of answers comprising answers to each question in the plurality of question hierarchies asked by the patient monitoring apparatus, the central computing system configured to determine a total point value, is the total point value being a sum of the point values assigned to each question that was asked by the patient monitoring apparatus, the central computing system further configured to determine a total earned point value, the total earned point value being a sum of all points assigned to questions to which an ambulatory patient provided answers that indicate particular pre-defined options, the central computing system further configured to determine a ratio between the total earned point value and the total point value and to notify a health care provider if the ratio exceeds a threshold.

37. A method of analyzing a set of answers to questions drawn from a plurality of question hierarchies, each question hierarchy in the plurality of question hierarchies corresponding to a symptom in a plurality of symptoms, the method comprising:

asking, at a patient monitoring apparatus, a first question in a first question hierarchy in the plurality of question hierarchies, the first question hierarchy corresponding to a first symptom in the plurality of symptoms;

receiving, at the patient monitoring apparatus, an answer to the first question, the first question soliciting information regarding the first symptom, the first question hierarchy including a second question, the second question soliciting additional information regarding the first symptom, each question in the first question hierarchy being assigned a point value, the first question hierarchy indicating that the second question is moot when the answer to the first question indicates a first option, the first question hierarchy indicating that the second question is not moot when the answer to the first question indicates a second option, making, at the patient monitoring apparatus, a decision based on the answer to the first question, the decision regarding whether the second question is moot in light of the answer to the first question;

automatically asking, at the patient monitoring apparatus, the second question when the patient monitoring apparatus makes the decision that the second question is not moot in light of the answer to the first question, the patient monitoring apparatus not asking the second question when the patient monitoring apparatus makes the decision that the second question is moot in light of the answer to the first question;

sending, by the patient monitoring apparatus, the set of answers to a central computing system, the set of answers comprising answers to each question in the question hierarchies asked by the patient monitoring apparatus, the central computing system configured to determine a number of points earned in each of the question hierarchies, the number of points earned for one of the question hierarchies based on a number of points assigned to questions in the ones of the question hierarchies to which the ambulatory patient provided answers that indicate particular pre-defined options and to notify a health care provider if the number of points earned within more than a pre-defined number of the question hierarchies crosses threshold values assigned to the question hierarchies.

* * * * *